(12) United States Patent
Chen et al.

(10) Patent No.: US 11,590,152 B2
(45) Date of Patent: Feb. 28, 2023

(54) TREATMENT OF HEARING LOSS

(71) Applicant: Massachusetts Eye and Ear Infirmary, Boston, MA (US)

(72) Inventors: Zheng-Yi Chen, Somerville, MA (US); Wenyan Li, Boston, MA (US); Yi-Zhou Quan, Dorchester, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 262 days.

(21) Appl. No.: 16/964,882

(22) PCT Filed: Jan. 28, 2019

(86) PCT No.: PCT/US2019/015348
§ 371 (c)(1),
(2) Date: Jul. 24, 2020

(87) PCT Pub. No.: WO2019/148067
PCT Pub. Date: Aug. 1, 2019

(65) Prior Publication Data
US 2021/0030775 A1    Feb. 4, 2021

Related U.S. Application Data

(60) Provisional application No. 62/622,598, filed on Jan. 26, 2018.

(51) Int. Cl.
*A61K 31/7028* (2006.01)
*A61K 31/19* (2006.01)
*A61K 31/365* (2006.01)
*A61K 45/06* (2006.01)

(52) U.S. Cl.
CPC .......... *A61K 31/7028* (2013.01); *A61K 31/19* (2013.01); *A61K 31/365* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,417,185 B1 | 7/2002 | Goff et al. |
| 6,489,344 B1 | 12/2002 | Nuss et al. |
| 6,541,466 B2 | 4/2003 | Wu et al. |
| 6,608,063 B2 | 8/2003 | Nuss et al. |
| 7,300,951 B2 | 11/2007 | Kreft et al. |
| 7,468,365 B2 | 12/2008 | Audia et al. |
| 7,544,511 B2 | 6/2009 | Yang et al. |
| 7,872,027 B2 | 1/2011 | Metallo et al. |
| 8,114,422 B2 | 2/2012 | Fujii et al. |
| 8,188,069 B2 | 5/2012 | Miller et al. |
| 8,226,943 B2 | 7/2012 | Gurney et al. |
| 8,338,482 B2 | 12/2012 | Chen et al. |
| 2004/0237127 A1 | 11/2004 | Zoghbi et al. |
| 2009/0258026 A2 | 10/2009 | Siebel et al. |
| 2011/0251120 A1 | 10/2011 | Wang |
| 2011/0305674 A1 | 12/2011 | Edge et al. |
| 2012/0107317 A1 | 5/2012 | Lau et al. |
| 2017/0071937 A1 | 3/2017 | Karp et al. |
| 2019/0203210 A1 | 7/2019 | Edge et al. |

FOREIGN PATENT DOCUMENTS

| | | |
|---|---|---|
| EP | 1949916 | 8/2011 |
| EP | 2487156 | 8/2012 |
| WO | WO 1998/028268 | 7/1998 |
| WO | WO 2002/047671 | 6/2002 |
| WO | WO 2004/090110 | 4/2005 |
| WO | WO 2009/005688 | 4/2009 |
| WO | WO 2009/040423 | 4/2009 |
| WO | WO 2012/080926 | 6/2012 |
| WO | 2017132530 | 8/2017 |
| WO | WO 2022/169881 | 8/2022 |

OTHER PUBLICATIONS

Zhao, S., Chen, C., Wang, S., Ji, F., & Xie, Y. (2016). MHY1485 activates mTOR and protects osteoblasts from dexamethasone. Biochemical and biophysical research communications, 481(3-4), 212-218. (Year: 2016).*
Jadali et al., "Activiation of P13K Signaling Prevents Aminoglycoside-Induced Hair Cell Death in the Murine Cochlea," Biology Open, 5:6 pp. 698-708, 2016.
Leitmeyer et al., "Inhibition of mTOR by Rapamycin Results in Auditory Hair Cell Damage and Decreased Spiral Ganglion Neuron Outgrowth and Neurite Formation In Vitro," BioMed Research International, vol. 2015, pp. 1-10, 2015.
Montcouquiol et al., "Intracellular Signals That Control Cell Proliferation in Mammalian Balance Epithelia: Key Roles for Phosphatidylinositol-3 Kinases, Mammalian Target of Rapamycin, and S6 Kinases in Preference to Calcium, Protein Kinase C, and Mitogen-Activated Protein Kinase," The Journal of Neuroscience, vol. 21, No. 2, pp. 570-580, 2001.
International Search Report and the Written Opinion from Corresponding PCT Application No. PCT/US2019/015348 dated Apr. 1, 2019, 9 pages.
Aggarwal et al., "Curcumin suppresses the paclitaxel-induced nuclear factor-kappaB pathway in breast cancer cells and inhibits lung metastasis of human breast cancer in nude mice," Clin. Cancer Res., Oct. 2005, 11(20):7490-7498.
Ahmed et al., "Eyal-Six1 interaction is sufficient to induce hair cell fate in the cochlea by activating Atoh1 expression in cooperation with Sox2," Dev. Cell., Feb. 2012, 22(2):377-390.

(Continued)

*Primary Examiner* — Dale R Miller
(74) *Attorney, Agent, or Firm* — Fish & Richardson P.C.

(57) ABSTRACT

Compositions for regeneration of inner cells and for treating hearing loss comprise at least one modulator of mechanistic target of rapamycin (mTOR) sufficient to induce reprogramming proliferation and regeneration of inner ear cells. The composition include, in some instances, an effective amount of one or more phosphatase and tensin homolog (PTEN) inhibitors, MYC/NOTCH modulators, Atonal Homolog 1 (Atoh1) modulators or combinations thereof.

7 Claims, 3 Drawing Sheets

(56) References Cited

OTHER PUBLICATIONS

Ashizawa et al., "Antitumor activity of a novel small molecule STAT3 inhibitor against a human lymphoma cell line with high STAT3 activation," Int. J. Oncol., Feb. 2011, 38(5):1245-1252.
CAS No. 1429639-50-8, "CZ415," SelleckChem, retrieved on Feb. 18, 2022, retrieved from URL <https://www.selleckchem.com/products/CZ415.html>, 3 pages.
CAS No. 154447-38-8, "LY 303511—CAS 154447-38-8—Calbiochem," Sigma-Aldrich, retrieved on Apr. 4, 2022, retrieved from URL <https://www.sigmaaldrich.com/US/en/product/mm/440203>, 6 pages.
CAS No. 159351-69-6, "Everolimus," Sigma-Aldrich, retrieved on Feb. 18, 2022, retrieved from URL <https://www.sigmaaldrich.com/US/en/substance/everolimus95822159351696>, 2 pages.
CAS No. 162635-04-3, "Temsirolimus," Sigma-Aldrich, retrieved on Apr. 5, 2022, retrieved from URL <https://www.sigmaaldrich.com/US/en/search/temsirolimus?focus=products&page=1&perpage=30&sort=relevance&term=temsirolimus&type=product>, 9 pages.
CAS No. 1660110-65-5, "SC-III3," BOC Sciences, retrieved on Apr. 5, 2022, retrieved from URL <https://www.bocsci.com/sc-iii3-cas-1660110-65-5-item-475933.html>, 7 pages.
CAS No. 1676893-24-5, "NSC781406," retrieved on Apr. 4, 2022, retrieved from URL <https://www.sigmaaldrich.com/US/en/product/targetmolchemicalsinc/ta9h9453348f?context=bbe>, 4 pages.
CAS No. 1685280-21-0, "DMH-25," MedKoo Biosciences Inc., retrieved on Feb. 18, 2022, retrieved from URL <https://www.medkoo.com/products/6774>, 2 pages.
CAS No. 1927857-61-1, "PQR530," Sigma-Aldrich, retrieved on Apr. 5, 2022, retrieved from URL <https://www.sigmaaldrich.com/US/en/product/achemblock/advh97ebf28f?context=bbe>, 4 pages.
CAS No. 326914-06-1, "MHY1485," Sigma Aldrich, retrieved on Feb. 18, 2022, retrieved from URL <https://www.sigmaaldrich.com/US/en/product/ambeedinc/ambh303c4b87?context=bbe>, 5 pages.
CAS No. 53123-88-9, "Rapamycin," Sigma-Aldrich, retrieved on Apr. 5, 2022, retrieved from URL <https://www.sigmaaldrich.com/US/en/product/sial/37094>, 8 pages.
CAS No. 572924-54-0, "Ridaforolimus," Sigma-Aldrich, retrieved on Apr. 5, 2022, retrieved from URL <https://www.sigmaaldrich.com/US/en/product/targetmolchemicalsinc/ta9h94533767?context=bbe>, 5 pages.
CAS No. 57818-44-7, "ABTL-0812," SelleckChem, retrieved on Feb. 18, 2022, retrieved from URL <https://www.selleckchem.com/products/abtl-0812.html>, 3 pages.
CAS No. 6724-53-4, "Perhexiline maleate salt," Sigma-Aldrich, retrieved on Apr. 5, 2022, retrieved from URL <https://www.sigmaaldrich.com/US/en/search/6724-53-4?focus=products&page=1&perpage=30&sort=relevance&term=6724-53-4&type=cas_number>, 8 pages.
CAS No. 853910-61-9, "NVP-BBD130," retrieved on Apr. 4, 2022, retrieved from URL <https://www.axonmedchem.com/product/1520>, 3 pages.
CAS No. 914913-88-5, "Palomid 529," retrieved on Apr. 4, 2022, retrieved from URL <https://www.sigmaaldrich.com/US/en/product/sigma/sm10801>, 6 pages.
Chan et al., "Notch signals positively regulate activity of the mTOR pathway in T-cell acute lymphoblastic leukemia," Blood, Jul. 2007, 110(1):278-286.
Cheng et al., "Promotion of Ovarian Follicle Growth following mTOR Activation: Synergistic Effects of AKT Stimulators," PLoS One, 2015, 10(2):e0117769, 9 pages.
Choi et al., "Inhibitory effect of mTOR activator MHY1485 on autophagy: suppression of lysosomal fusion," PLoS One, 2012, 7(8):e43418, 10 pages.
Chung et al., "CD19 is a major B cell receptor-independent activator of MYC-driven B-lymphomagenesis," J. Clin. Invest., Jun. 2012, 122(6):2257-2266.
Churcher et al., "Design and Synthesis of Highly Potent Benzodiazepine γ-Secretase Inhibitors: Preparation of (2 S ,3 R )-3-(3,4-Difluorophenyl)-2-(4-fluorophenyl)-4-hydroxy-N-((3 S )-1-methyl-2-oxo-5-phenyl-2,3-dihydro-1 H-benzo[ e ][1,4]-diazepin-3-yl)butyramide by Use of an Asymmetric Ireland-Claisen Rearrangement," J. Med. Chem., Jun. 2003, 46(12):2275-2278.
Clausen et al., "In vitro cytotoxicity and in vivo efficacy, pharmacokinetics, and metabolism of 10074-G5, a novel small-molecule inhibitor of c-Myc/Max dimerization," J. Pharmacol. Exp. Ther., Dec. 2010, 335(3):715-727.
Engelhard et al., "Inhibitory effects of phenylbutyrate on the proliferation, morphology, migration and invasiveness of malignant glioma cells," J. Neurooncol., Apr. 1998, 37(2):97-108.
Extended European Search Report in European Appln. No. 19744493.8, dated Oct. 19, 2021, 8 pages.
Fauq et al., "A Multigram Chemical Synthesis of the γ-Secretase Inhibitor LY411575 and its Diastereoisomers," Bioorg Med Chem Lett, Oct. 2010, 17(22):6392-5.
Fernandez et al., "Membrane Interactions of Antimicrobial Peptides from Australian Frogs," Biochimica et Biophysica Acta (BBA)—Biomembranes, Aug. 2009, 1788(8):1630-1638.
Fuwa et al., "Synthesis of Biotinylated Photoaffinity Probes Based on Arylsulfonamide γ-Secretase Inhibitors," Bioorg Med Chem Lett, Aug. 2006, 16(16):4184-9.
Ge & Ren, "mTOR-STAT3-notch signalling contributes to ALDH2-induced protection against cardiac contractile dysfunction and autophagy under alcoholism," J Cell Mol Med, Mar. 2012, 16(3):615-626.
Ge et al., "Identification of a novel MTOR activator and discovery of a competing endogenous RNA regulating autophagy in vascular endothelial cells," Autophagy, Jun. 2014, 10(6):957-71.
GenBank Accession No. NC_000010.11, "*Homo sapiens* chromosome 10, GRCh38.p13 Primary Assembly," dated Jun. 6, 2016, 3 pages.
GenBank Accession No. NM_000435.2, "*Homo sapiens* notch 3 (NOTCH3), mRNA," dated Feb. 21, 2016, 6 pages.
GenBank Accession No. NM_002467.4, "*Homo sapiens* v-myc avian myelocytomatosis viral oncogene homolog (MYC), mRNA," dated Sep. 15, 2016, 4 pages.
GenBank Accession No. NM_005172.1, "*Homo sapiens* atonal bHLH transcription factor 1 (ATOH1), mRNA," dated Oct. 6, 2016, 3 pages.
GenBank Accession No. NM_005378.4, "*Homo sapiens* v-myc avian myelocytomatosis viral oncogene neuroblastoma derived homolog (MYCN), transcript variant 2, mRNA," dated Mar. 15, 2015, 4 pages.
GenBank Accession No. NM_017617.3, "*Homo sapiens* notch 1 (NOTCH1), mRNA," dated Feb. 10, 2016, 8 pages.
GenBank Accession No. NM_024408.3, "*Homo sapiens* notch 2 (NOTCH2), transcript variant 1, mRNA," dated Oct. 6, 2016, 7 pages.
GenBank Accession No. NM_145178.3, "*Homo sapiens* atonal bHLH transcription factor 7 (ATOH7), mRNA," dated Jun. 21, 2015, 3 pages.
GenBank Accession No. NP_000426.2, "neurogenic locus notch homolog protein 3 precursor [*Homo sapiens*]," dated Feb. 21, 2016, 4 pages.
GenBank Accession No. NP_002458.2, "myc proto-oncogene protein isoform 1 [*Homo sapiens*]," dated Sep. 15, 2016, 3 pages.
GenBank Accession No. NP_004548.3, "neurogenic locus notch homolog protein 4 preproprotein [*Homo sapiens*]," dated Oct. 9, 2016, 4 pages.
GenBank Accession No. NP_005163.1, "protein atonal homolog 1 [*Homo sapiens*]," dated Oct. 6, 2016, 3 pages.
GenBank Accession No. NP_005369.2, "N-myc proto-oncogene protein isoform 1 [*Homo sapiens*]," dated Sep. 4, 2011, 3 pages.
GenBank Accession No. NP_060087.3, "neurogenic locus notch homolog protein 1 preproprotein [*Homo sapiens*]," dated Feb. 10, 2016, 5 pages.
GenBank Accession No. NP_077719.2, "neurogenic locus notch homolog protein 2 isoform 1 preproprotein [*Homo sapiens*]," dated Oct. 6, 2016, 4 pages.
GenBank Accession No. NP_660161.1, "transcription factor ATOH7 [*Homo sapiens*]," dated Jun. 21, 2015, 3 pages.
Genbank Accession No. AK021874.1, "*Homo sapiens* cDNA FLJ11812 fis, clone HEMBA1006364," dated Jan. 9, 2008, 2 pages.

(56) References Cited

OTHER PUBLICATIONS

GenBank Acession No. NC_000004.12, "*Homo sapiens* chromosome 4, GRCh38.p13 Primary Assembly," dated Jun. 6, 2016, 3 pages.
GenBank Acession No. NM_004557.3, "*Homo sapiens* notch 4 (NOTCH4), mRNA," dated Oct. 9, 2016, 6 pages.
Gera et al., "AKT activity determines sensitivity to mammalian target of rapamycin (mTOR) inhibitors by regulating cyclin D1 and c-myc expression," J Biol Chem, Jan. 2004, 279(4)2737-2746.
Gonzalez-Mariscal et al., "ZO-2, a tight junction protein involved in gene expression, proliferation, apoptosis, and cell size regulation," Annals of the New York Academy of Sciences, Jun. 2017, 1397(1):35-53.
Hu et al., "Induction of Differentiation of β-cell Leukemia Cell Lines JVM-2 and EHEB by Bryostatin 1," Leuk Lymphoma, Jun. 1992, 10(1-2): 135-42.
Huang et al., "A Small-molecule c-Myc Inhibitor, 10058-F4, Induces Cell-cycle Arrest, Apoptosis, and Myeloid Differentiation of Human Acute Myeloid, Leukemia" Exp Hematol, Nov. 2006, 34(11):1480-9.
Hurley et al., "Modulating the Functional Contributions of c-Myc to the Human Endothelial Cell Cyclic Strain Response," J Vasc Res, Sep. 2009, 47(1):80-90.
Imbimbo, "Therapeutic Potential of γ-Secretase Inhibitors and Modulators," Curr Top Med Chem, 2008, 8(1):54-61.
International Preliminary Report on Patentability in International Appln. No. PCT/US2019/015348, dated Jul. 28, 2020, 8 pages.
International Search Report and Written Opinion in International Appln. No. PCT/US2019/015348, dated Apr. 1, 2019, 9 pages.
International Search Report and Written Opinion in International Appln. No. PCT/US2022/14952, dated May 12, 2022, 10 pages.
Ishikawa et al., "Opposing Functions of Fbxw7 in Keratinocyte Growth, Differentiation and Skin Tumorigenesis Mediated Through Negative Regulation of c-Myc and Notch," Oncogene, 2013, 32:1921-32.
Ladu et al., "E2F1 inhibits c-Myc-driven apoptosis via PIK3CNAkt/mTOR and COX-2 in a mouse model of human liver cancer," Gastroenterology, Oct. 2008, 135:1322-1332.
Lamming, "Inhibition of the Mechanistic Target of Rapamycin (mTOR)-Rapamycin and Beyond," Cold Spring Harb Perspect Med, 2016, 6:a025924: 15 pages.
Lauber et al., "The Cooked Food Derived Carcinogen 2-amino-1-methyl-6-phenylimidazo [4,5-b] pyridine is a Potent Oestrogen: A Mechanistic Basis for its Tissue-specific Carcinogenicity," Carcinogenesis, Dec. 2004, 25(12):2509-17.
Leitmeyer et al., "Inhibition of mTOR by Rapamycin Results in Auditory Hair Cell Damage and Decreased Spiral Ganglion Neuron Outgrowth and Neurite Formation In Vitro," BioMed Research International, Mar. 2015, 2015(2):1-10.
Lin et al., "Small-molecule c-Myc Inhibitor, 10058-F4, Inhibits Proliferation, Downregulates Human Telomerase Reverse Transcriptase and Enhances Chemosensitivity in Human Hepatocellular Carcinoma Cells," Anticancer Drugs, Feb. 2007, 18(2):161-70.
Masui et al., "mTOR complex 2 controls glycolytic metabolism in glioblastoma through FoxO acetylation and upregulation of c-Myc," Cell Metab, Nov. 2013, 18(5):726-739.
Matsushita et al., "Novel diagnosis and therapy for hepatoma targeting HBV-related carcinogenesis through alternative splicing of FIR (PUF60)/FIR[del]exon2," Hepatoma Research, Sep. 2018, 4(61): 1-17.
McEwan et al., "Cohesion is Required for Activation of MYC by Esterdiol," PLoS One, Nov. 2012, 7(11):e49160, 14 pages.
Moon et al., "WNT and β-catenin Signalling: Diseases and Therapies," Nat Rev Genet, Sep. 2004, 5(9):689-699.
Mori et al., "Chemoprevention by Naturally Occurring and Synthetic Agents in Oral, Liver, and Large Bowel Carcinogenesis," J Cell Biochem Suppl, 1997, 27:35-41.
Page et al., "Small Molecule STAT5-SH2 Domain Inhibitors Exhibit Potent Antileukemia Activity," J Med Chem, Feb. 2012, 55(3):1047-1055.
Park et al., "Inhibition of AP-1 Transcription Activator Induces Myc-Dependent Apoptosis in HL60 Cells," J Cell Biochem, Apr. 2004, 91(5):973-986.
Purow, "Notch Inhibition as a Promising New Approach to Cancer Therapy," Adv Exp Med Biol, 2012, 727:305-19.
Sai et al., "Induction of Cell-cycle Arrest and Apoptosis in Glioblastoma Stem-like Cells by WP1193, a Novel Small Molecule Inhibitor of the JAK2/STAT3 Pathway," J Neurooncol, May 2012, 107(3):487-501.
Samon et al., "Preclinical Analysis of the γ-Secretase Inhibitor PF-03084014 in Combination with Glucocorticoids in T-Cell Acute Lymphoblastic Leukemia," Mol Cancer Ther, Jul. 2012, 11(7):1565-75.
Shih and Wang, "Notch Signaling, γ-Secretase Inhibitors, and Cancer Therapy," Cancer Res, Mar. 2007, 67(5):1879-82.
Shu et al., "Renewed proliferation in adult mouse cochlea and regeneration of hair cells," Nature Communications, 2019, 10:5530, 15 pages.
Smetanina et al., "Ortho-aminoazotoluene Activates Mouse Constitutive Androstane Receptor (mCAR) and Increases Expression of mCAR Target Genes," Toxicol Appl Pharmacol, Aug. 2011, 255(1):76-85.
UniProt Accession No. P60484, "RecName: Full=Phosphatidylinositol 3,4,5-trisphosphate 3-phosphatase and dual-specificity protein phosphatase PTEN; AltName: Full=Mutated in multiple advanced cancers 1; AltName: Full=Phosphatase and tensin homolog," Nov. 30, 2016, 28 pages.
Weihofen et al., "Identification of Signal Peptide Peptidase, a Presenilin-type Aspartic Protease," Science, Jun. 2002, 296(5576):2215-8.
Zhang et al., "Orally Bioavailable Small-molecule Inhibitor of Transcription Factor STAT3 Regresses Human Breast and Lung Cancer Xenografts," Proc Natl Acad Sci USA, Jun. 2012, 109(24):9623-8.
Zhang et al., "PI3K/AKT/mTOR Signaling Mediates Valproic Acid-Induced Neuronal Differentiation of Neural Stem Cells through Epigenetic Modifications," Stem Cell Reports, May 2017, 8:1256-1269.

\* cited by examiner

TREATMENT OF HEARING LOSS

CROSS-REFERENCE TO RELATED APPLICATIONS

This application is a National Stage Application filed under 35 U.S.C. § 371, of International Patent Application No PCT/US2019/015348, filed on Jan. 28, 2019, which claims the benefit of and priority to U.S. Provisional Application No. 62/622,598, filed on Jan. 26, 2018, the entire contents of which are incorporated herein by reference in their entirety.

STATEMENT OF FEDERAL FUNDING

This invention was made with government support under Grant No. RO1 DC006908, awarded by the National Institutes of Health. The Government has certain rights in the invention.

FIELD OF THE INVENTION

Embodiments of the invention are directed to compositions for inner ear cell regeneration. In particular, compositions comprise modulators of mechanistic target of rapamycin (mTOR). Methods of treatment include the use of these modulators of mTOR.

BACKGROUND

One of the most common types of hearing loss is sensorineural deafness that is caused by the loss of hair cells or hair cell function. Hair cells are sensory cells in the cochlea responsible for transduction of sound into an electrical signal. The human inner ear contains only about 15,000 hair cells per cochlea at birth, and, although these cells can be lost as a result of various genetic or environmental factors (e.g., noise exposure, ototoxic drug toxicity, viral infection, aging, and genetic defects), the lost or damaged cells cannot be replaced. Hair cells also are found in the utricle of the vestibule, an organ which regulates balance. Therefore, hair cell regeneration is an important approach to restoring hearing and vestibular function.

SUMMARY

Embodiments of the invention are directed to compositions for inner ear cell regeneration and uses thereof.

In certain embodiments, a method of regenerating inner ear cells in mature mammalian cochlea in a subject in need thereof, comprises contacting an inner ear cell with an effective amount of at least one activator of mechanistic target of rapamycin (mTOR) sufficient to induce reprogramming proliferation and regeneration of inner ear cells.

In certain embodiments, a method of regenerating inner ear cells in mature mammalian cochlea in a subject in need thereof, comprising contacting an inner ear cell with an effective amount of at least one modulator of mechanistic target of rapamycin (mTOR) sufficient to induce reprogramming proliferation and regeneration of inner ear cells and/or one or more MYC/NOTCH modulators, Atonal Homolog 1 (Atoh1) modulators or combinations thereof.

In certain embodiments, a method of treating hearing loss in a subject comprises contacting an inner ear cell with an effective amount of at least one activator of mechanistic target of rapamycin (mTOR) sufficient to induce reprogramming proliferation and regeneration of inner ear cells and/or one or more phosphatase and tensin homolog (PTEN) inhibitors.

In certain embodiments, a method of treating hearing loss in a subject comprises contacting an inner ear cell with an effective amount of at least one modulator of mechanistic target of rapamycin (mTOR) sufficient to induce reprogramming proliferation and regeneration of inner ear cells and/or one or more modulators of expression and/or activity of Atoh1.

In certain embodiments, a method of treating hearing loss in a subject comprises contacting an inner ear cell with an effective amount of at least one activator of mechanistic target of rapamycin (mTOR) sufficient to induce reprogramming proliferation and regeneration of inner ear cells and/or one or more MYC/NOTCH modulators, Atoh-1 modulators or combinations thereof.

In certain embodiments, the method of treating hearing loss or regeneration of inner ear cells further comprises administering one or more phosphatase and tensin homolog (PTEN) inhibitors, MYC/NOTCH modulators, Atoh-1 modulators or combinations thereof.

In certain embodiments, the inner ear cells comprise: inner ear cells comprise: stria vascularis, hair cells, supporting cells or ganglion neurons.

In certain embodiments, an mTOR activator comprises sodium valproate (VPA), mhy1485, 3-benzyl-5-((2-nitrophenoxy) methyl)-dihydrofuran-2(3H)-one (3BDO), salidroside, phosphatidic acid, antibodies, antibody fragments, oligonucleotides, polynucleotides, antisense oligonucleotides, siRNAs, enzymes, gene editing agents, nucleases, peptides, polypeptides, small molecules, synthetic compounds, natural compounds or combinations thereof.

In certain embodiments, the one or more PTEN inhibitors comprise: bpV(phen), bpV(pic), VO-OHpic, SF1670, antibodies, antibody fragments, oligonucleotides, polynucleotides, antisense oligonucleotides, siRNAs, enzymes, gene editing agents, nucleases, peptides, polypeptides, small molecules, synthetic compounds, natural compounds or combinations thereof.

In certain embodiments, a composition comprises an effective amount of at least one mechanistic target of rapamycin (mTOR) activator. In certain embodiments, an mTOR activator comprises sodium valproate (VPA), mhy1485, 3-benzyl-5-((2-nitrophenoxy) methyl)-dihydrofuran-2(3H)-one (3BDO), salidroside, phosphatidic acid, antibodies, antibody fragments, oligonucleotides, polynucleotides, antisense oligonucleotides, siRNAs, enzymes, gene editing agents, nucleases, peptides, polypeptides, small molecules, synthetic compounds, natural compounds or combinations thereof. In certain embodiments, the composition further comprises an effective amount of one or more: phosphatase and tensin homolog (PTEN) inhibitors, MYC/NOTCH modulators, Atoh-1 modulators or combinations thereof.

In certain embodiments, a composition comprises an effective amount of at least one activator of mechanistic target of rapamycin (mTOR) and an inducer of expression of Atoh1.

Other aspects are described infra.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

As used herein, the term "agent" or "modulator" is meant to encompass any molecule, chemical entity, composition, drug, therapeutic agent, chemotherapeutic agent, or biological agent capable of modulating expression or activity of a desired molecule e.g. mTOR, MYC, Notch, preventing, ameliorating, or treating a disease or other medical condition. The term includes small molecule compounds, antisense reagents, siRNA reagents, antibodies, enzymes, peptides organic or inorganic molecules, natural or synthetic compounds and the like. An agent can be assayed in accordance with the methods of the invention at any stage during clinical trials, during pre-trial testing, or following FDA-approval.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid. "Analogs" in reference to nucleosides includes synthetic nucleosides having modified base moieties and/or modified sugar moieties, e.g., described generally by Scheit, Nucleotide Analogs, John Wiley, New York, 1980; Freier & Altmann, *Nucl. Acid. Res.*, 1997, 25(22), 4429-4443, Toulmé, J. J., *Nature Biotechnology* 19:17-18 (2001); Manoharan M., *Biochemica et Biophysica Acta* 1489:117-139(1999); Freier S. M., Nucleic Acid Research, 25:4429-4443 (1997), Uhlman, E., *Drug Discovery & Development*, 3: 203-213 (2000), Herdewin P., *Antisense & Nucleic Acid Drug Dev.*, 10:297-310 (2000)); 2'-O, 3'-C-linked [3.2.0] bicycloarabinonucleosides (see e.g. N. K Christiensen., et al., *J. Am. Chem. Soc.*, 120: 5458-5463 (1998). Such analogs include synthetic nucleosides designed to enhance binding properties, e.g., duplex or triplex stability, specificity, or the like.

The term "antibody" or "immunoglobulin" is intended to encompass both polyclonal and monoclonal antibodies. The preferred antibody is a monoclonal antibody reactive with the antigen. The term "antibody" is also intended to encompass mixtures of more than one antibody reactive with the antigen (e.g., a cocktail of different types of monoclonal antibodies reactive with the antigen). The term "antibody" is further intended to encompass whole antibodies, biologically functional fragments thereof, single-chain antibodies, and genetically altered antibodies such as chimeric antibodies comprising portions from more than one species, bifunctional antibodies, antibody conjugates, humanized and human antibodies. Biologically functional antibody fragments, which can also be used, are those peptide fragments derived from an antibody that are sufficient for binding to the antigen. "Antibody" as used herein is meant to include the entire antibody as well as any antibody fragments (e.g. $F(ab')_2$, Fab', Fab, Fv) capable of binding the epitope, antigen, or antigenic fragment of interest.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA. An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, short, hairpin RNA (shRNA), therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

As used herein, the terms "associated with," "conjugated," "linked," "attached," and "tethered," when used with respect to two or more moieties, means that the moieties or domains are physically associated or connected with one another, either directly or via one or more additional moieties that serves as a linking agent, to form a structure that is sufficiently stable so that the moieties remain physically associated under the conditions in which the structure is used, e.g., physiological conditions. The term "connected" will be used for the sake of brevity and is meant to include all possible methods of physically associating each domain of the chimeric molecule to each other. For example, a supercharged protein is typically associated with or connected to a nucleic acid by a mechanism that involves non-covalent binding (e.g., electrostatic interactions). In certain embodiments, a positively charged, supercharged protein is associated with a nucleic acid through electrostatic interactions to form a complex. In some embodiments, a sufficient number of weaker interactions can provide sufficient stability for moieties to remain physically associated under a variety of different conditions. In certain embodiments, the agent to be delivered is covalently bound to the supercharged protein.

As used herein "Atoh1" refers to atonal homolog 1 and family thereof. The Atoh1 belongs to the basic helix-loop-helix (BHLH) family of transcription factors. It activates E-box dependent transcription along with E47. The full-length Atoh1 appears, for example, in the NCBI protein database under accession no. NC_000004.12. See, also, US Publication Nos. US 20040237127 and US 20110251120.

The term "co-administer" refers to the simultaneous presence of two active agents in the blood of an individual. Active agents that are co-administered can be concurrently or sequentially delivered.

The terms "determining", "measuring", "evaluating", "detecting", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As defined herein, an "effective" amount of a compound or agent (i.e., an effective dosage) means an amount sufficient to produce a (e.g., clinically) desirable result.

The term "expression" as used herein is defined as the transcription and/or translation of a particular nucleotide sequence driven by its promoter.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full length polypeptides and nucleic acid, respectively. A nucleic acid fragment of almost any length is employed. For example, illustrative polynucleotide segments with total lengths of about 10,000, about 5,000, about 3,000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

As used herein, the term "inhibitor of" or "inhibitory agent" e.g. of PTEN, is meant to encompass any molecule, chemical entity, composition, drug, therapeutic agent, chemotherapeutic agent, or biological agent capable of preventing, ameliorating, or treating a dysfunction or other medical condition. The term includes small molecule compounds, antisense oligonucleotides, siRNA reagents, antibodies, antibody fragments bearing epitope recognition sites, such as Fab, Fab', F(ab')2 fragments, Fv fragments, single chain antibodies, antibody mimetics (such as DARPins, affibody molecules, affilins, affitins, anticalins, avimers, fynomers, Kunitz domain peptides and monobodies), peptoids, aptamers; enzymes, gene editing agents, nucleases, peptides organic or inorganic molecules, natural or synthetic compounds and the like. An agent can be assayed in accordance with the methods of the invention at any stage during clinical trials, during pre-trial testing, or following FDA-approval. The invention includes antibodies or fragments of such antibodies, so long as they exhibit the desired biological activity. Also included in the invention are chimeric antibodies, such as humanized antibodies. Generally, a humanized antibody has one or more amino acid residues introduced into it from a source that is non-human. Humanization can be performed, for example, using methods described in the art, by substituting at least a portion of a rodent complementarity-determining region for the corresponding regions of a human antibody.

By "marker" is meant any protein or polynucleotide having an alteration in expression level or activity that is associated with a disease or disorder.

By the term "modulate," it is meant that any of the mentioned activities, are, e.g., increased, enhanced, increased, agonized (acts as an agonist), promoted, decreased, reduced, suppressed blocked, or antagonized (acts as an agonist). Therefore, a "modulator" can be an agonist or an antagonist. Whether the modulator is an agonist or antagonist is clear from the context by which it is referred to herein. Modulation can increase activity more than 1-fold, 2-fold, 3-fold, 5-fold, 10-fold, 100-fold, etc., over baseline values. Modulation can also decrease its activity below baseline values. Modulation can also normalize an activity to a baseline value.

As used herein, "MYC" refers to the MYC family of transcription factors. MYC is a multifunctional, nuclear phosphoprotein that plays a role in cell cycle progression, apoptosis and cellular transformation. The full length sequence of human MYC appears, for example, in the NCBI protein database under accession no. NP_002458.2. MYC functions as a transcription factor that regulates transcription of specific target genes. Mutations, overexpression, rearrangement and translocation of this gene have been associated with a variety of hematopoietic tumors, leukemias and lymphomas, including Burkitt lymphoma. MYC is also known in the art as MYC, v-MYC myelocytomatosis viral oncogene homolog (avian), transcription factor p64, bHLHe39, MRTL, avian myelocytomatosis viral oncogene homolog, v-MYC avian myelocytomatosis viral oncogene homolog, MYC proto-oncogene protein, class E basic helix-loop-helix protein 39, MYC-related translation/localization regulatory factor, and proto-oncogene MYC, and BHLHE39.

As used herein, the term, "NOTCH" refers to the NOTCH family of signaling proteins, which includes NOTCH 1, NOTCH 2, NOTCH 3 and NOTCH 4, or NOTCH intracellular domain (NICD). The full length sequence of human NOTCH1 appears, for example, in the NCBI protein database under accession no. NP_060087.3 (see ncbi.nlm.nih.gov). Members of this Type 1 transmembrane protein family share structural characteristics including an extracellular domain consisting of multiple epidermal growth factor-like (EGF) repeats, and an intracellular domain consisting of multiple, different domain types. NOTCH family members play a role in a variety of developmental processes by controlling cell fate decisions. NOTCH 1 is cleaved in the trans-Golgi network, and presented on the cell surface as a heterodimer. NOTCH 1 functions as a receptor for membrane bound ligands Jagged 1, Jagged 2 and Delta 1 to regulate cell-fate determination. Upon ligand activation through the released NOTCH intracellular domain (NICD) it forms a transcriptional activator complex with RBPJ/RBP-SUH and activates genes of the enhancer of split locus. NOTCH 1 affects the implementation of differentiation, proliferation and apoptotic programs.

As used herein, a "nucleic acid" or "nucleic acid sequence" or "cDNA" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs, and refers to nucleic acid sequences in which one or more introns have been removed. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, for instance, DNA which is part of a hybrid gene encoding additional polypeptide sequences.

As used herein, the terms "nucleic acid sequence", "polynucleotide," and "gene" are used interchangeably throughout the specification and include complementary DNA (cDNA), linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. The nucleic acid sequences may be "chimeric" that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide. These sequences typically comprise at least one region wherein the sequence is modified in order to exhibit one or more desired properties.

In the present context, the terms "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleobases described in Benner et al., U.S. Pat. No. 5,432,272. The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

As used herein, "nucleoside" includes the natural nucleosides, including 2'-deoxy and 2'-hydroxyl forms, e.g., as described in Kornberg and Baker, DNA Replication, 2nd Ed. (Freeman, San Francisco, 1992).

"Optional" or "optionally" means that the subsequently described event or circumstance can or cannot occur, and that the description includes instances where the event or circumstance occurs and instances where it does not.

As used in this specification and the appended claims, the term "or" is generally employed in its sense including "and/or" unless the content clearly dictates otherwise.

The terms "patient" or "individual" or "subject" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

As used herein, a "pharmaceutically acceptable" component/carrier etc. is one that is suitable for use with humans and/or animals without undue adverse side effects (such as toxicity, irritation, and allergic response) commensurate with a reasonable benefit/risk ratio.

As used herein, "phosphatase and tensin homolog" (PTEN) is a protein that, in humans, is encoded by the PTEN gene. Mutations of this gene are a step in the development of many cancers. Genes corresponding to PTEN (orthologs) have been identified in most mammals for which complete genome data are available. PTEN acts as a tumor suppressor gene through the action of its phosphatase protein product. This phosphatase is involved in the regulation of the cell cycle, preventing cells from growing and dividing too rapidly. The protein encoded by this gene is a phosphatidylinositol-3,4,5-trisphosphate 3-phosphatase. It contains a tensin-like domain as well as a catalytic domain similar to that of the dual specificity protein tyrosine phosphatases. Unlike most of the protein tyrosine phosphatases, this protein preferentially dephosphorylates phosphoinositide substrates. It negatively regulates intracellular levels of phosphatidylinositol-3,4,5-trisphosphate in cells and functions as a tumor suppressor by negatively regulating Akt/PKB signaling pathway. The DNA sequence can be found under accession number NC_000010.11. The protein sequence can be found under UniProtKB/Swiss-Prot for PTEN Gene P60484.

As used herein, unless otherwise indicated, the terms "peptide", "polypeptide" or "protein" are used interchangeably herein, and refer to a polymer of amino acids of varying sizes. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or be naturally occurring. This term also includes polypeptides that have been modified or derivatized, such as by glycosylation, acetylation, phosphorylation, and the like.

A "polynucleotide" means a single strand or parallel and anti-parallel strands of a nucleic acid. Thus, a polynucleotide may be either a single-stranded or a double-stranded nucleic acid.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

As defined herein, a "therapeutically effective" amount of a compound or agent (i.e., an effective dosage) means an amount sufficient to produce a therapeutically (e.g., clinically) desirable result, for example, induce cell cycle reentry and/or proliferation of the cells of the inner ear (e.g., a hair cell or a supporting cell). The cells are contacted with amounts of the active agent effective to induce cell cycle reentry and/or proliferation and/or transdifferentiation of supporting cells to hair cells. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

The term "target nucleic acid" refers to a nucleic acid (often derived from a biological sample), to which the oligonucleotide is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding oligonucleotide directed to the target. The term target nucleic acid may refer to the specific subsequence of a larger nucleic acid to which the oligonucleotide is directed or to the overall sequence (e.g., gene or mRNA) whose expression level it is desired to detect. The difference in usage will be apparent from context.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Where any nucleotide or amino acid sequence is specifically referred to by a Swiss Prot. or GENBANK Accession number, the sequence is incorporated herein by reference. Information associated with the accession number, such as identification of signal peptide, extracellular domain, transmembrane domain, promoter sequence and translation start, is also incorporated herein in its entirety by reference.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In preferred embodiments, the genes, nucleic acid sequences, amino acid sequences, peptides, polypeptides and proteins are human.

General Techniques

For further elaboration of general techniques useful in the practice of this invention, the practitioner can refer to standard textbooks and reviews in cell biology, tissue culture, embryology, and physiology.

With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in vitro (M. V. Wiles, *Meth. Enzymol.* 225:900, 1993); Properties and uses of Embryonic Stem Cells: Prospects for Application to Human Biology and Gene Therapy (P. D. Rathjen et al., *Reprod. Fertil. Dev.* 10:31, 1998).

BRIEF DESCRIPTION OF THE DRAWINGS

FIGS. 1A-1O are a series of fluorescent stains and graphs demonstrating that mTOR is downstream of the MYC/NICD co-activation pathway. (FIG. 1A) A diagram illustrating the procedure of Dox and rapamycin treatment on adult rtTA/tet-MYC/tet-NICD cochlea in vitro. (FIGS. 1B-B") Phospho-rpS6 (p-rpS6), a downstream effector of mTOR signaling, was not detected in freshly dissected adult cochlea. SOX2 labeled SCs. (FIGS. 1C-1C''') 6 days after Dox treatment of the adult rtTA/tet-MYC/tet-NICD cochlea in vitro, EdU$^+$ and p-rpS6$^+$ cells were observed in the sensory epithelial region (SE) and limbus region (Lib). Arrows pointed to SOX2$^+$/EdU$^+$/p-rpS6$^+$ cells. (FIGS. 1D-1D''') 6 days after Dox and mTOR inhibitor rapamycin treatment of the adult rtTA/tet-MYC/tet-NICD cochlea in vitro, the numbers of EdU$^+$ and p-rpS6$^+$ cells in the SE and Lib decreased significantly. (FIGS. 1E, 1F) Quantification of p-rpS6$^+$ and EdU$^+$ cells in the cultured adult rtTA/tet-MYC/tet-NICD cochleae exposed to DOX, with or without rapamycin treatment, showed a significant reduction in p-rpS6$^+$ and EdU$^+$ cells after rapamycin treatment in the sensory epithelial and limbus regions. *$p<0.05$, ****$p<0.0001$, Student's t-test. Error bar, mean±SEM; n=5. (FIG. 1G) A diagram illustrating the study of rapamycin treatment on HC induction by Atoh1. (FIGS. 1H-1I''') The numbers of EdU$^+$ cells and new HCs in the SE and Lib were significantly decreased in the rapamycin-treated adult rtTA/tet-MYC/tet-NICD cochleae following 3-day Dox treatment and ad-Atoh1 infection for 14 days. (FIG. 1J) Quantification of total HCs and ectopic HCs (MYO7A$^+$) in the mid-base turn of cochleae from h-i showed a significant reduction in HC numbers in the SE and Lib regions. *$p<0.05$, **$p<0.01$, Student's t-test. Error bar, mean±SEM; n=5. (FIG. 1K) A diagram illustrating the study of the effect of mTOR activator MHY1485 on proliferation and HC regeneration. (FIG. 1L-1M") Significantly more EdU$^+$ cells and new HCs in SE and Lib in the mid-base turn were observed in the MHY1485-treated adult rtTA/tet-NICD cochlea following 3-day Dox treatment and ad-Atoh1 infection for 14 days, compared to DMSO-treated controls. (FIGS. 1N-1O) Quantification of EdU$^+$ cells, MYO7A$^+$ HCs and ectopic HCs in 1-m". *$p<0.05$, Student's t-test. Error bar, mean±SEM; n=5. Scale bars: 10 μm.

FIG. 2A: In cultured adult wildtype (WT) cochlea infected with ad-ATOH1 for 14 days, no proliferating cell was induced. Limited hair cell regeneration was seen (PVALB$^+$/MYO7a$^+$). FIG. 2B: In cultured WT adult cochlea treated with MHY1485 and infected with ad-ATOH1, numerous proliferating cells (EdU$^+$) and enhanced hair cell regeneration (PVALB$^+$/MYO7a$^+$) were seen. FIG. 2C. In cultured adult rtTA/tet-NICD cochlea treated with DOX to activate NICD, MHY1485 to induce mTOR and ad-ATOH1 to induce hair cell regeneration, most proliferating cells and hair cells were seen.

DETAILED DESCRIPTION

Figures 1A, 1B, 1C, 1D, 1E, 1F, 1G:
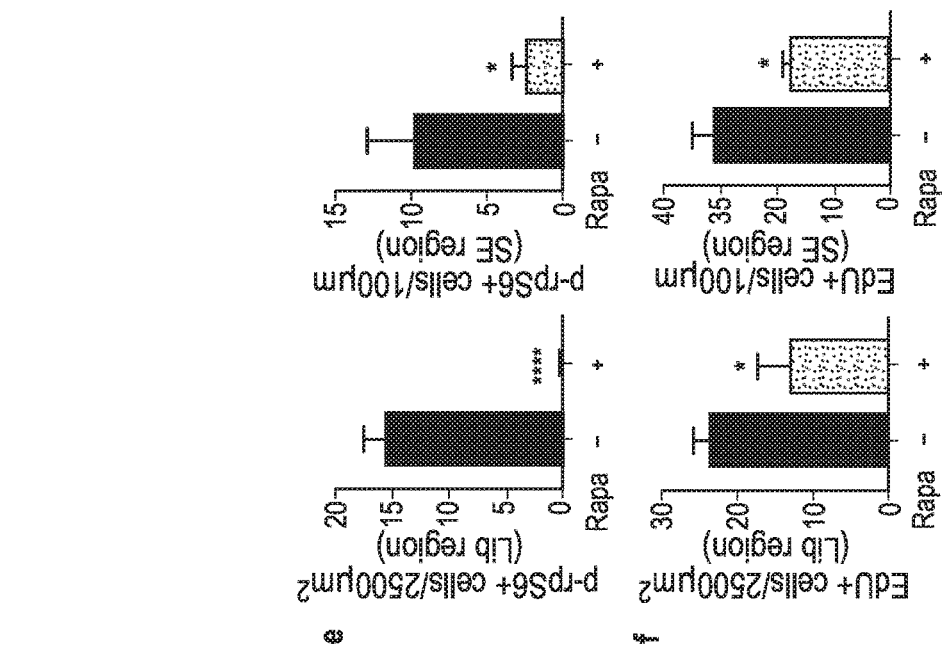

Complete quiescence state of adult mammalian cochlea makes it particularly challenging to induce proliferation. Renewed proliferation in mature inner ear could provide the opportunities to regenerate diverse cochlear cell types whose functions are essential to hearing. The invention is based in part on the finding that the mechanistic target of rapamycin (mTOR) which is downstream of MYC/NOTCH pathway and plays a role for MYC/NOTCH mediated proliferation in adult/mature inner ear. This is shown by renewed proliferation in adult/mature mammalian inner ear induced by activation of mTOR by an mTOR activator compound MYH1485 and NOTCH activation. The results herein show that mTOR activation alone is sufficient to induce proliferation in adult/mature mammalian inner ear; mTOR and NOTCH activation enhances proliferation as well as ATOH1-mediated hair cell regeneration, an indication of synergistic interaction between mTOR and NOTCH.

Compositions and Treatments

Hearing loss affects a large portion of population yet no treatment is available beyond hearing aids and cochlear implant, both of which provide limited benefits. In the US alone, over 30 million people suffer from hearing loss. The major cause of hearing loss in humans is due to irreversible loss of the inner ear sensory cells, hair cells, which are responsible for detecting sounds and sensing balance. As the result, regeneration of hair cells has become a focus aiming at developing potential therapy for hearing loss. Further hearing loss can be caused by defective cell types in the inner ear such as stria vascularis and supporting cells, neurons, or any cell type associated with deafness or associated disorders thereof, whose regeneration could lead to restoration of hearing.

Accordingly, embodiments are directed to compositions for treating hearing loss, for inducing proliferation or cell cycle reentry of inner ear cells, such as, for example, stria vascularis, hair cells and supporting cells. Methods of regeneration of inner ear cells, supporting cells, neurite growth, and treatment of hearing loss are also described.

In certain embodiments, a composition comprises an effective amount of least one mechanistic target of rapamycin (mTOR) activator. In certain embodiments, an mTOR activator comprises sodium valproate (VPA), mhy1485, 3-benzyl-5-((2-nitrophenoxy) methyl)-dihydrofuran-2(3H)-one (3BDO), salidroside, phosphatidic acid, antibodies, antibody fragments, oligonucleotides, polynucleotides, antisense oligonucleotides, siRNAs, enzymes, gene editing agents, nucleases, peptides, polypeptides, small molecules, synthetic compounds, natural compounds or combinations thereof. In certain embodiments, the composition further comprises an effective amount of one or more: phosphatase and tensin homolog (PTEN) inhibitors, MYC/NOTCH modulators, Atoh-1 modulators or combinations thereof.

In certain embodiments, a composition comprises an effective amount of at least one activator of mechanistic target of rapamycin (mTOR) and an inducer of expression of Atoh1.

In general, the compositions further comprise agents or MYC/NOTCH modulators which increase MYC, NOTCH or both MYC activity and NOTCH activity within the cell sufficient to induce proliferation or cell cycle reentry of the hair cells and/or supporting cells.

Administration of the mTOR compositions embodied herein, can lead to regeneration of cells within the stria vascularis that includes marginal cells, intermediate cells, basal cells and fibrocytes. Degeneration of stria vascularis causes hearing loss. Regeneration of any of the cell types could lead to hearing recovery, including neurite growth or other neural cells associated with hearing and hearing loss due to any cause. Hair cells are inner ear sensory cells, including inner hair cells, outer hair cells, and vestibular hair cells. Supporting cells include Deiters cells, Hensen cells, Pillar cells, inner phalangeal cells, inner border cells, Claudius cells, border cells, basal cells, interdental cells, inner sulcus, spiral limbus.

In certain embodiments, the mTOR modulators, the phosphatase and tensin homolog (PTEN) inhibitors, MYC/NOTCH modulators, Atoh-1 modulators or combinations thereof are proteins or peptides. In certain embodiments a composition comprises a therapeutically effective amount of an mTOR modulator, PTEN modulators, MYC protein or peptides, MYC modulators, NOTCH protein or peptides, NOTCH Intracellular domain (NICD) proteins or peptides, Atonal Homolog 1 (Atoh1), Atoh1 modulators, transcription factors, transcription modulators, or combinations thereof.

For efficient protein delivery, proteins need to enter cells with sufficient amount, and are released from endosomes within cells and reach the targets. Improvement in the endosome release would have drastic effects on the amount of protein to reach the target with enhanced biological effect. Accordingly, in embodiments, the compositions comprising proteins or peptides are linked to antimicrobial or membrane destabilizing peptides, for example, aurein, mutants or variants thereof. Membrane destabilization peptides are known in the art. See, for example, Fernandez, D. I. et al., *Biochim. Biophys. Acta*, 2009 August; 1788(8):1630-8.

In certain embodiments, a membrane destabilizing domain comprises one or more of: antimicrobial or membrane destabilizing proteins or peptides, polynucleotides, oligonucleotides, bacterial or viral (e.g. reovirus outer capsid protein or peptide, μ1; papilloma virus capsid protein or peptide L2; etc.), antibacterial molecules, antimicrobial peptides, microtubules, lipids, synthetic or natural molecules, or combinations thereof. Antimicrobial peptides (AMPs) are a class of membrane-active peptides that penetrate microbial membranes to provide defense against bacteria, fungi, and viruses, often with high selectivity (Zasloff, M. Nature 2002, 415, 389).

In an embodiment, the modulators embodied herein are encapsulated in a liposome. In one embodiment, the liposome is a cationic liposome.

In an embodiment, a method of regenerating inner ear cells in vitro or in vivo comprises contacting a cell in vitro or administering to an inner ear of a patient in need of such treatment, In certain embodiments, a method of regenerating inner ear cells in mature mammalian cochlea in a subject in need thereof, comprises contacting an inner ear cell with an effective amount of at least one activator of mechanistic target of rapamycin (mTOR) sufficient to induce reprogramming proliferation and regeneration of inner ear cells.

In certain embodiments, a method of regenerating inner ear cells in mature mammalian cochlea in a subject in need thereof, comprising contacting an inner ear cell with an effective amount of at least one modulator of mechanistic target of rapamycin (mTOR) sufficient to induce reprogramming proliferation and regeneration of inner ear cells and/or one or more MYC/NOTCH modulators, Atonal Homolog 1 (Atoh1) modulators or combinations thereof.

In certain embodiments, a method of treating hearing loss in a subject comprises contacting an inner ear cell with an effective amount of at least one activator of mechanistic target of rapamycin (mTOR) sufficient to induce reprogramming proliferation and regeneration of inner ear cells and/or one or more phosphatase and tensin homolog (PTEN) inhibitors.

In certain embodiments, a method of treating hearing loss in a subject comprises contacting an inner ear cell with an effective amount of at least one modulator of mechanistic target of rapamycin (mTOR) sufficient to induce reprogramming proliferation and regeneration of inner ear cells and/or one or more modulators of expression and/or activity of Atoh1.

In certain embodiments, a method of treating hearing loss in a subject comprises contacting an inner ear cell with an effective amount of at least one activator of mechanistic target of rapamycin (mTOR) sufficient to induce reprogramming proliferation and regeneration of inner ear cells and/or one or more MYC/NOTCH modulators, Atoh-1 modulators or combinations thereof.

In certain embodiments, the method of treating hearing loss or regeneration of inner ear cells further comprises administering one or more phosphatase and tensin homolog (PTEN) inhibitors, MYC/NOTCH modulators, Atoh-1 modulators or combinations thereof.

In certain embodiments, an mTOR activator comprises sodium valproate (VPA), mhy1485, 3-benzyl-5-((2-nitrophenoxy) methyl)-dihydrofuran-2(3H)-one (3BDO), salidroside, phosphatidic acid or combinations thereof. In certain embodiments, the one or more PTEN inhibitors comprise: bpV(phen), bpV(pic), VO-OHpic, SF1670, antibodies, antibody fragments, oligonucleotides, polynucleotides, antisense oligonucleotides, siRNAs, enzymes, gene editing agents, nucleases, peptides, polypeptides, small molecules, synthetic compounds, natural compounds or combinations thereof.

In certain embodiments, the inner ear cells comprise: inner ear cells comprise: stria vascularis, hair cells, supporting cells or ganglion neurons.

The method may also include the step of inhibiting MYC and/or NOTCH activity after proliferation of the inner ear cells, such as, stria vascularis, hair or supporting cell to induce differentiation or transdifferentiation of the cell and/ or at least one of its daughter cells into a hair cell. The method may also further include the step of activating Atoh1 to induce transdifferentiation of the supporting cells to hair cells. The MYC activity in the hair and/or supporting cells is increased by administering an effective amount of MYC protein, MYC peptides or MYC activators. The NOTCH activity is increased by administering an effective amount of NOTCH protein, NOTCH peptides, NOTCH activators, NOTCH Intracellular domain (NICD) proteins, NOTCH Intracellular domain (NICD) peptides, or combinations thereof. Inhibition of MYC and/or NOTCH can be accomplished through administration of inhibitors or once the activator has degraded over time. Activation of Atoh1 is accomplished by the delivery of Atoh1 proteins, Atoh1 peptides, Atoh1 activators, or combinations thereof.

Also disclosed is a method for reducing the loss of, maintaining, or promoting hearing in a subject. The method comprises contacting an inner ear cell with an effective amount of at least one activator of mechanistic target of rapamycin (mTOR) sufficient to induce reprogramming proliferation and regeneration of inner ear cells and/or one or more activators which: increases MYC activity, NOTCH activity, or both MYC activity and NOTCH activity, as appropriate, within a hair cell and/or a supporting cell of the inner ear thereby to induce cell proliferation to produce daughter cells, and, after cell proliferation, decreasing MYC and/or NOTCH activity, and administering a composition embodied herein, comprising Atoh1 activators to induce daughter cells of hair cell origin to differentiate into hair cells or permitting daughter cells of supporting cell origin to transdifferentiate into hair cells thereby to reduce the loss of, maintain or promote hearing in the subject. The daughter cells of supporting cell origin can be induced to transdifferentiate into hair cells by activating Atoh1 activity, for example, by gene expression, by administration of an effective amount of Atoh1 or an Atoh1 agonist. The steps can be performed in vivo (for example, in the inner ear of a mammal, in particular in the cochlea), or ex vivo, wherein the resulting cells are cultured and/or introduced into the inner ear of the subject. In certain embodiments, the method of treating hearing loss or regeneration of inner ear cells further comprises administering one or more phosphatase and tensin homolog (PTEN) inhibitor.

In certain embodiments, the methods and compositions described herein can be used to promote growth of neurites from the ganglion neurons of the inner ear. For example, the regeneration of hair cells may promote the growth of new neurites from ganglion neurons and formation of new synapses with the regenerated hair cells to transmit sound and balance signals from the hair cells to the brain. In some embodiments, the methods and compositions described herein can be used to reestablish proper synaptic connections between hair cells and auditory neurons to treat, for example, auditory neuropathy.

Subjects with sensorineural hair cell loss experience the degeneration of cochlea hair cells, which frequently results in the loss of spiral ganglion neurons in regions of hair cell loss. Such subjects may also experience loss of supporting cells in the organ of Corti, and degeneration of the limbus, spiral ligament, and stria vascularis in the temporal bone material.

In certain embodiments, the present invention can be used to treat hair cell loss and any disorder that arises as a consequence of cell loss in the ear, such as hearing impairments, deafness, vestibular disorders, tinnitus (see, Kaltenbach et al. (2002) *J. Neurophysiol.* 88(2):699-714s), and hyperacusis (Kujawa et al. (2009) *J. Neurosci.* 29(45): 14077-14085), for example, by promoting differentiation (e.g., complete or partial differentiation) of one or more cells into one or more cells capable of functioning as sensory cells of the ear, e.g., hair cells.

In certain embodiments, the subject can have sensorineural hearing loss, which results from damage or malfunction of the sensory part (the cochlea) or non-sensory part (the limbus, spiral ligament and stria vascularis) or the neural part (the auditory nerve) of the ear, or conductive hearing loss, which is caused by blockage or damage in the outer and/or middle ear. Alternatively or in addition, the subject can have mixed hearing loss caused by a problem in both the conductive pathway (in the outer or middle ear) and in the nerve pathway (the inner ear). An example of a mixed hearing loss is a conductive loss due to a middle-ear infection combined with a sensorineural loss due to damage associated with aging.

In certain embodiments, the subject may be deaf or have a hearing loss for any reason, or as a result of any type of event. For example, a subject may be deaf because of a genetic or congenital defect; for example, a human subject can have been deaf since birth, or can be deaf or hard-of-hearing as a result of a gradual loss of hearing due to a genetic or congenital defect. In another example, a human subject can be deaf or hard-of-hearing as a result of a traumatic event, such as a physical trauma to a structure of the ear, or a sudden loud noise, or a prolonged exposure to loud noises. For example, prolonged exposures to concerts, airport runways, and construction areas can cause inner ear damage and subsequent hearing loss.

In certain embodiments, a subject can experience chemical-induced ototoxicity, wherein ototoxins include therapeutic drugs including antineoplastic agents, salicylates, quinines, and aminoglycoside antibiotics, contaminants in foods or medicinals, and environmental or industrial pollutants.

In certain embodiments, a subject can have a hearing disorder that results from aging. Alternatively or in addition, the subject can have tinnitus (characterized by ringing in the ears) or hyperacusis (heightened sensitivity to sound).

In addition, the methods and compositions described herein can be used to treat a subject having a vestibular dysfunction, including bilateral and unilateral vestibular dysfunction. Vestibular dysfunction is an inner ear dysfunction characterized by symptoms that include dizziness, imbalance, vertigo, nausea, and fuzzy vision and may be accompanied by hearing problems, fatigue and changes in cognitive functioning. Vestibular dysfunction can be the result of a genetic or congenital defect; an infection, such as a viral or bacterial infection; or an injury, such as a traumatic or nontraumatic injury. Vestibular dysfunction is most commonly tested by measuring individual symptoms of the disorder (e.g., vertigo, nausea, and fuzzy vision).

Alternatively or in addition, the methods and compositions described herein can be used prophylactically, such as to prevent, reduce or delay progression of hearing loss, deafness, or other auditory disorders associated with loss of inner ear function. For example, a composition containing one or more of the agents can be administered with (e.g., before, after or concurrently with) a second composition, such as an active agent that may affect hearing loss. Such ototoxic drugs include the antibiotics neomycin, kanamycin, amikacin, viomycin, gentamycin, tobramycin, erythromycin, vancomycin, and streptomycin; chemotherapeutics such as cisplatin; nonsteroidal anti-inflammatory drugs (NSAIDs) such as choline magnesium trisalicylate, diclofenac, diflunisal, fenoprofen, flurbiprofen, ibuprofen, indomethacin, ketoprofen, meclofenamate, nabumetone, naproxen, oxaprozin, phenylbutazone, piroxicam, salsalate, sulindac, and tolmetin; diuretics; salicylates such as aspirin; and certain malaria treatments such as, quinine and chloroquine. For example, a human undergoing chemotherapy can be treated using the compounds and methods described herein. The chemotherapeutic agent cisplatin, for example, is known to cause hearing loss. Therefore, a composition containing one or more agents that modulate mTOR expression or activity o can be administered with cisplatin therapy (e.g., before, after or concurrently with) to prevent or lessen the severity of the cisplatin side effect. Such a composition can be administered before, after and/or simultaneously with the second therapeutic agent. The two agents may be administered by different routes of administration.

In certain embodiments, the methods and compositions described herein can be used to increase the levels (e.g., protein levels) and/or activity (e.g., biological activity) of mTOR, MYC and NOTCH in cells (e.g., inner ear cells) and inhibit PTEN expression or activity. Exemplary methods and compositions include, but are not limited to methods and compositions for increasing MYC or NOTCH expression (e.g., transcription and/or translation) or levels (e.g., concentration) in cells. It is contemplated that such modulation can be achieved in hair cells and/or supporting cells in vivo and ex vivo.

mTOR Activators: In certain embodiments, a composition comprises an effective amount of at least one mechanistic target of rapamycin (mTOR) activator. In certain embodiments, an mTOR activator comprises sodium valproate (VPA), mhy1485, 3-benzyl-5-((2-nitrophenoxy) methyl)-dihydrofuran-2(3H)-one (3BDO), salidroside, phosphatidic acid, antibodies, antibody fragments, oligonucleotides, polynucleotides, antisense oligonucleotides, siRNAs, enzymes, gene editing agents, nucleases, peptides, polypeptides, small molecules, synthetic compounds, natural compounds or combinations thereof. In certain embodiments, an mTOR activator or mTOR signal pathway activator comprises MHY1485 (CAS Number: 326914-06-1; Calbiochem, Burlington, Mass.). Other mTOR activators comprise: sodium valproate (VPA), phosphatidic acid, propranolol, 3-benzyl-5-((2-nitrophenoxy) methyl)-dihydrofuran-2(3H)-one (3BDO), FLJ11812(GenBank accession number AK021874.1) (Ge D, Han L, Huang S, et al. Identification of a novel MTOR activator and discovery of a competing endogenous RNA regulating autophagy in vascular endothelial cells. Autophagy. 2014; 10(6):957-71).

mTOR inhibitors, include for example, CZ415 (CAS no.: 1429639-50-8), LY 303511 (CAS no.: 154447-38-8), Everolimus (CAS no.: 159351-69-6), Temsirolimus (CAS no.: 162635-04-30), SC-III3 (CAS no.: 1660110-65-5), NSC781406 (CAS no.: 1676893-24-5), DMH-25 (CAS no.: 1685280-21-0), PQR530 (CAS no.: 1927857-61-1), Rapamycin (CAS no.: 3123-88-9), Ridaforolimus (CAS no.: 572924-54-0), ABTL-0812 (CAS no.: 57818-44-7), Perhexiline maleate salt (CAS no.: 6724-53-4), NVP-BBD130 (CAS no.: 853910-61-90, Palomid 529 (CAS no.: 914913-88-5). See, BOC Sciences Shirley, NY.

PTEN inhibitors: PTEN inhibitors in the present invention refer to all substances that have the function to inhibit the action of the PTEN (Phosphatase and Tensin Homolog Deleted from Chromosome 10) gene or PTEN protein. The PTEN gene is located on chromosome 10q23.3 and it is identified as a tumor suppression factor. PTEN protein is widely expressed throughout the cells of the entire body and it is known as an enzyme catalyzing the dephosphorylation reaction of phosphatidylinositol 3,4,5-trisphosphate; PIP3 which is an inositol phospholipid. Moreover, PIP3 is synthesized intracellularly by PI3 kinase (PI3K) and induces the activation of protein kinase B (PKB)/AKT. PTEN is responsible for the dephosphorylation reaction of this PIP3 and it is believed to have an action of converting PIP3 into a phosphatidylinositol 4,5-bisphosphate; PIP2. Therefore, PTEN negatively regulates the PI3K/AKT signal transduction pathway. When the activity of PTEN is inhibited, PIP3 accumulates in the cells, and thus, results in the activation of the PI3K/AKT signal transduction pathway.

The PTEN inhibitors comprise compounds containing vanadium, for example, includes pV(phenbig)bis peroxo (phenyl biguanide)oxovanadium dipotassium) or HOpic (bpV)bis peroxo(5-hydroxypyridine-2-carboxy)oxovanadium dipotassium, VO-OHPic trihydrate((OC-6-45)Aqua(3-hydroxy-2-piperidinecarboxylato-kapaN1, kapaO$_2$) [3-(hydroxy-kapaO)-2-piperidinecarboxylato(2-)-kapaO$_2$]oxovanadate(1-), hydrogen trihydrate), and the like. These may be used alone, or two or more kinds may be used in combination. In certain embodiments, the one or more PTEN inhibitors comprise: bpV(phen), bpV(pic), VO-OHpic, SF1670, antibodies, antibody fragments, oligonucleotides, polynucleotides, antisense oligonucleotides, siRNAs, enzymes, gene editing agents, nucleases, peptides, polypeptides, small molecules, synthetic compounds, natural compounds or combinations thereof.

PTEN inhibitory agents useful in the methods of the invention can be small molecules, but can also be enzymes and/or nucleic acid molecules, e.g., antisense, gene-editing agents, ribozyme, or RNA interference technology, e.g., siRNA molecules corresponding to a portion of the nucleotide sequence encoding PTEN.

In certain embodiments, a PTEN inhibitory agent decreases expression of PTEN by at least 1, 2, 3, 4, 5 7, 10, 15, 20, 25, 30, 40 50 60, 70, 80, 90 or 100 percent relative to the same test assay in the absence of the PTEN inhibitory agent (control). The inhibition of PTEN can be measured using commercially available kits or use of commercial screening services.

In some embodiments, the inhibitory agent comprises an antibody or fragment thereof (e.g. anti-PTEN antibody), a binding protein, a polypeptide, or any combination thereof. In some embodiments, the inhibitory agent comprises a small molecule. In some embodiments, the inhibitory agent comprises a nucleic acid molecule. In some embodiments, the oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), a short interfering RNA (siRNA), a micro, interfering RNA (miRNA), a small, temporal RNA (stRNA), a short, hairpin RNA (shRNA), mRNA, nucleic acid sequences comprising one or more modified nucleobases or backbones, or combinations thereof.

Antisense polynucleotides may act by directly blocking translation by hybridizing to mRNA transcripts or degrading such transcripts of a gene e.g. PTEN, cytokines released by senescent cells, etc. The antisense molecule may be recombinantly made using at least one functional portion of a gene in the antisense orientation as a region downstream of a promoter in an expression vector. Chemically modified bases or linkages may be used to stabilize the antisense polynucleotide by reducing degradation or increasing half-life in the body (e.g., methyl phosphonates, phosphorothioate, peptide nucleic acids). The sequence of the antisense molecule may be complementary to the translation initiation site (e.g., between −10 and +10 of the target's nucleotide sequence).

siRNA refers to double-stranded RNA of at least 20-25 basepairs which mediates RNA interference (RNAi). Duplex siRNA corresponding to a target RNA may be formed by separate transcription of the strands, coupled transcription from a pair of promoters with opposing polarities, or annealing of a single RNA strand having an at least partially self-complementary sequence. Alternatively, duplexed oligoribonucleotides of at least about 21 to about 23 basepairs may be chemically synthesized (e.g., a duplex of 21 ribonucleotides with 3' overhangs of two ribonucleotides) with some substitutions by modified bases being tolerated. Mismatches in the center of the siRNA sequence, however, abolishes interference. The region targeted by RNA interference should be transcribed, preferably as a coding region of the gene. Interference appears to be dependent on cellular factors (e.g., ribonuclease III) that cleave target RNA at sites 21 to 23 bases apart; the position of the cleavage site appears to be defined by the 5' end of the guide siRNA rather than its 3' end. Priming by a small amount of siRNA may trigger interference after amplification by an RNA-dependent RNA polymerase.

Nucleases: Any suitable nuclease system can be used including, for example, Argonaute family of endonucleases, clustered regularly interspaced short palindromic repeat (CRISPR) nucleases, zinc-finger nucleases (ZFNs), transcription activator-like effector nucleases (TALENs), meganucleases, other endo- or exo-nucleases, or combinations thereof. See Schiffer, 2012, J Virol 88(17):8920-8936, incorporated by reference. In certain embodiments, the system is an Argonaute nuclease system.

CRISPR-Cas: In certain aspects, inhibition of, for example, PTEN can be achieved by administration of inhibitory nucleic acids (e.g., dsRNAs, siRNAs, antisense oligonucleotides, etc.) directed to inhibit PTEN or any other cytokine expression or activity. It is also contemplated that CRISPR-Cas (e.g., CRISPR-Cas9) methods can be used to excise and/or replace sections of genes encoding regulators of extracellular cytokine bioavailability Such methods can be performed upon the cells of a subject in vivo or ex vivo. Use of any combination of the above and/or other known inhibitor of PTEN is also contemplated. The CRISPR-Cas system is known in the art. Non-limiting aspects of this system are described in U.S. Pat. No. 8,697,359, issued Apr. 15, 2014, the entire content of which is incorporated herein by reference.

Non-limiting examples of Cas proteins include Cas1, Cas1B, Cas2, Cas3, Cas4, Cas5, Cas6, Cas7, Cas8, Cas9 (also known as Csn1 and Csx12), Cas 10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments, the CRISPR enzyme is Cas9, and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the invention, nickases may be used for genome editing via homologous recombination.

A guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

Argonautes: Argonautes are a family of endonucleases that use 5' phosphorylated short single-stranded nucleic acids as guides to cleave targets (Swarts, D. C. et al. The evolutionary journey of Argonaute proteins. *Nat. Struct. Mol. Biol.* 21, 743-753 (2014)). Similar to Cas9, Argonautes have key roles in gene expression repression and defense against foreign nucleic acids (Swarts, D. C. et al. *Nat. Struct. Mol. Biol.* 21, 743-753 (2014); Makarova, K. S., et al. *Biol. Direct* 4, 29 (2009). Molloy, S. *Nat. Rev. Microbiol.* 11, 743 (2013); *Vogel, J. Science* 344, 972-973 (2014). Swarts, D. C. et al. *Nature* 507, 258-261 (2014); Olovnikov, I., et al. *Mol.*

Cell 51, 594-605 (2013)). However, Argonautes differ from Cas9 in many ways (Swarts, D. C. et al. *Nat. Struct. Mol. Biol.* 21, 743-753 (2014)). Cas9 only exist in prokaryotes, whereas Argonautes are preserved through evolution and exist in virtually all organisms; although most Argonautes associate with single-stranded (ss)RNAs and have a central role in RNA silencing, some Argonautes bind ssDNAs and cleave target DNAs (Swarts, D. C. et al. *Nature* 507, 258-261 (2014); Swarts, D. C. et al. *Nucleic Acids Res.* 43, 5120-5129 (2015)). guide RNAs must have a 3' RNA-RNA hybridization structure for correct Cas9 binding, whereas no specific consensus secondary structure of guides is required for Argonaute binding; whereas Cas9 can only cleave a target upstream of a PAM, there is no specific sequence on targets required for Argonaute. Once Argonaute and guides bind, they affect the physicochemical characteristics of each other and work as a whole with kinetic properties more typical of nucleic-acid-binding proteins (Salomon, W. E., et al. *Cell* 162, 84-95 (2015)).

If desired, the polynucleotides of the invention may also be used with a microdelivery vehicle such as cationic liposomes and adenoviral vectors. For a review of the procedures for liposome preparation, targeting and delivery of contents, see Mannino and Gould-Fogerite, *BioTechniques,* 6:682 (1988). See also, Felgner and Holm, Bethesda Res. Lab. Focus, 11(2):21 (1989) and Maurer, R. A., Bethesda Res. Lab. Focus, 11(2):25 (1989).

Antibodies: These molecules can be generated by any method known in the art. Antibodies can be generated not only against the desired molecule but also to the receptor thereby preventing engagement by the ligand, e.g. anti-PTEN antibodies, anti-PTEN receptor antibodies etc.

The term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')2, and Fab. F(ab')2, and Fab fragments that lack the Fc fragment of intact antibody, clear more rapidly from the circulation, and may have less non-specific tissue binding of an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv), fusion polypeptides, and unconventional antibodies. As used herein, the term "single-chain variable fragment" or "scFv" is a fusion protein of the variable regions of the heavy (VH) and light chains (VL) of an immunoglobulin covalently linked to form a VH:VL heterodimer. The heavy (VH) and light chains (VL) are either joined directly or joined by a peptide-encoding linker (e.g., 10, 15, 20, 25 amino acids), which connects the N-terminus of the VH with the C-terminus of the VL, or the C-terminus of the VH with the N-terminus of the VL. In some embodiments, the linker includes glycine for flexibility, and serine or threonine for solubility. scFv proteins retain the specificity of the original immunoglobulin. Single chain Fv antibodies can be expressed as described by Huston, et al. (*Proc. Nat. Acad. Sci. USA,* 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., *Hybidoma* (Larchmt) 2008 27(6):455-51; Peter et al., *J Cachexia Sarcopenia Muscle* 2012 Aug. 12; Shieh et al., *J Imunol* 2009 183(4):2277-85; Giomarelli et al., *Thromb Haemost* 2007 97(6):955-63; Fife et al., *J Clin Invst* 2006 116(8):2252-61; Brocks et al., *Immunotechnology* 1997 3(3): 173-84; Moosmayer et al., *Ther Immunol* 1995 2(10: 31-40). Agonistic scFvs having stimulatory activity have been described (see, e.g., Peter et al., *J Biol Chem* 2003 25278(38):36740-7; Xie et al., *Nat Biotech* 1997 15(8):768-71; Ledbetter et al., *Crit Rev Immunol* 1997 17(5-6):427-55; Ho et al., *BioChim Biophys Acta* 2003 1638(3):257-66).

MYC, NOTCH, or Atoh1 Polypeptides: It is contemplated that MYC, NOTCH, and Atoh1 proteins, including full length proteins, biologically active fragments, and homologs of MYC and NOTCH can be introduced into target cells using techniques known in the art.

Exemplary MYC polypeptides include, for example, NP_002458.2, as referenced in the NCBI protein database. Exemplary NOTCH polypeptides include, for example, NP_060087.3, as referenced in the NCBI protein database.

Exemplary Atoh1 polypeptides include, for example, NP 005163.1, as referenced in the NCBI protein database.

In certain embodiments, nucleic acid sequences encoding MYC, NOTCH, and Atoh1 family members may be used in accordance with the methods described herein. Exemplary MYC family members include N-MYC, referenced in the NCBI protein database as NP_005369.2. Exemplary NOTCH family members include NOTCH2, referenced in the NCBI protein database as NP_077719.2; NOTCH3, referenced in the NCBI protein database as NP_000426.2; and NOTCH4, referenced in the NCBI protein database as NP_004548.3. Exemplary Atoh1 family members include Atoh7, referenced in the NCBI protein database as NP_660161.1.

In certain embodiments, a protein sequence of the invention may comprise a consensus protein sequence or a nucleotide sequence encoding a consensus protein sequence. Consensus protein sequences of MYC, NOTCH intracellular domain, and Atoh1 of the invention are set forth below. The MYC, NOTCH, or Atoh1 polypeptides can be used in combination with compositions to enhance uptake of the polypeptides into biological cells. In certain embodiments, the Atoh1, MYC, or NOTCH polypeptides can be mutated to include amino acid sequences that enhance uptake of the polypeptides into a biological cell. In certain embodiments, Atoh1, MYC, or NOTCH polypeptides can be altered or mutated to increase the stability and/or activity of the polypeptide (e.g., MYC, NOTCH or Atoh1 point mutants). In certain embodiments, MYC, NOTCH or Atoh1 polypeptides can be altered to increase nuclear translocation of the polypeptide. In certain embodiments, altered MYC, NOTCH or Atoh1 polypeptides or biologically active fragments of MYC, NOTCH, or Atoh1 retain at least 50%, 60%, 70%, 80%, 90%, or 95% of the biological activity of full length, wild type respective c-MYC, NOTCH or Atoh1 protein in the species that is the same species as the subject that is or will be treated with the methods and compositions described herein.

In certain embodiments, MYC polypeptides sequences can be 50%, 60%, 70%, 80%, 85%, 90%, 95%, 98%, 99%, or 100% identical to NP_002458.2. In certain embodiments, NOTCH polypeptides sequences are 50%, 60%, 70%, 80%, 85%, 90%, 95%, 98%, 99%, or 100% identical to NP_060087.3. In certain embodiments, Atoh1 polypeptides sequences can be 50%, 60%, 70%, 80%, 85%, 90%, 95%, 98%, 99%, or 100% identical to NP_005163.1. In certain embodiments, agents encoded by modified Atoh1, MYC, NICD, or NOTCH nucleic acid sequences and Atoh1, MYC, or NOTCH polypeptide sequences possess at least a portion of the activity (e.g., biological activity) of the molecules encoded by the corresponding, e.g., unmodified, full-length Atoh1, MYC, or NOTCH nucleic acid sequences and Atoh1, MYC, or NOTCH polypeptide sequences. For example, molecules encoded by modified Atoh1, MYC, or NOTCH nucleic acid sequences and modified Atoh1, MYC, or NOTCH polypeptides retain 50%, 60%, 70%, 80%, 85%, 90%, 95%, 98%, 99%, or 100% of the activity (e.g., biological activity) of the molecules encoded by the corresponding, e.g., unmodified, respective Atoh1, MYC, or NOTCH nucleic acid sequences and/or full length Atoh1, MYC, or NOTCH polypeptide sequences.

In certain embodiments, the MYC and NOTCH proteins of the invention can be administered to cells as a single protein containing both MYC and NOTCH (or active domains thereof), preferably separated by a cleavable linker. Examples of cleavable linkers are known in the art (see, e.g., U.S. Pat. Nos. 5,258,498 and 6,083,486.)

MYC, NOTCH or Atoh1 levels (e.g., protein levels) and/or activity (e.g., biological activity) in target cells and/or in the nucleus of target cells can be assessed using standard methods such as Western Blotting, in situ hybridization, reverse transcriptase polymerase chain reaction, immunocytochemistry, viral titer detection, and genetic reporter assays. Increases in MYC, NOTCH or Atoh1 levels (e.g., protein levels) and/or activity (e.g., biological activity) in target cells and/or in the nucleus of target cells can be assessed by comparing MYC, NOTCH or Atoh1 levels and/or activity in a first cell sample or a standard with MYC, NOTCH or Atoh1 levels and/or activity in a second cell sample, e.g., contacting the cell sample with an agent contemplated to increase MYC, NOTCH or Atoh1 levels and/or activity.

Atoh1, MYC, or NOTCH Polynucleotides, Oligonucleotides: Atoh1, MYC, or NOTCH can be expressed in target cells using one or more expression constructs known in the art. Such expression constructs include, but are not limited to, naked DNA, viral and non-viral expression vectors. Exemplary MYC nucleic acid sequences that may be expressed in target cells include, for example, NM_002467.4, as referenced in the NCBI gene database. Exemplary NOTCH nucleic acid sequences that may be expressed include, for example, NM_017617.3, as referenced in the NCBI gene database. Exemplary Atoh1 nucleic acid sequences that may be expressed in target cells include, for example, NM_005172.1, as referenced in the NCBI gene database.

In certain embodiments, MYC, NOTCH, and Atoh1 family members may be used. Exemplary MYC family members include N-MYC, referenced in the NCBI gene database as NM_005378.4. Exemplary NOTCH family members include NOTCH2, referenced in the NCBI gene database as NM_024408.3; NOTCH3, referenced in the NCBI gene database as NM_000435.2; and NOTCH4, referenced in the NCBI gene database as NM_004557.3. Exemplary Atoh1 family members include Atoh7, referenced in the NCBI gene database as NM_145178.3.

In certain embodiments, DNA encoding MYC, NOTCH or Atoh1 can be an unmodified wild type sequence. Alternatively, DNA encoding MYC, NOTCH or Atoh1 can be modified using standard techniques. For example, DNA encoding MYC, NOTCH or Atoh1 can be modified or mutated, e.g., to increase the stability of the DNA or resulting polypeptide. Polypeptides resulting from such altered DNAs should retain the biological activity of wild type MYC, NOTCH or Atoh1. In certain embodiments, DNA encoding Atoh1, MYC, or NOTCH can be altered to increase nuclear translocation of the resulting polypeptide. In certain embodiments, DNA encoding MYC, NOTCH or Atoh1 can be modified using standard molecular biological techniques to include an additional DNA sequence that can encode one or more of, e.g., detectable polypeptides, signal peptides, and protease cleavage sites.

In certain embodiments, MYC nucleic acid sequences can be 50%, 60%, 70%, 80%, 85%, 90%, 95%, 98%, 99%, or 100% identical to NM_002467.4. In certain embodiments, NOTCH nucleic acid sequences are 50%, 60%, 70%, 80%, 85%, 90%, 95%, 98%, 99%, or 100% identical to NM_017617.3. In certain embodiments, Atoh1 nucleic acid sequences are 50%, 60%, 70%, 80%, 85%, 90%, 95%, 98%, 99%, or 100% identical to NM_005172.1.

MYC, NOTCH or Atoh1 Pathway Modulators: In certain embodiments, MYC or NOTCH levels (e.g., protein levels) and/or activity (e.g., biological activity) can be increased or decreased using compounds or compositions that target MYC or NOTCH, or one or more components of the MYC or NOTCH pathway. Accordingly, in some embodiments, inhibiting NOTCH and activating Atoh1 comprises suppression of any one or more NOTCH1 targets, such as Hes5 and Hes1, both of which act as antagonists to Atoh1. Such suppression can be achieved by any conventional means, including, for example, anti-sense oligonucleotides against Hes1 and Hes5, or by delivering proteins that suppress Hes function. In some embodiments, any one or more molecules associated with the pathways of MYC, NOTCH, Atoh1 are targeted. Similarly, Atoh1 levels (e.g., protein levels) and/or activity (e.g., biological activity) can be increased using compounds that target Atoh1 or one or more components of the Atoh1 pathway.

Exemplary MYC activators include microRNAs that target FBXW-7 (Ishikawa Y et al, Oncogene 2012 Jun. 4; doi: 10.1038/onc.2012.213) and activators that increase MYC expression levels or activity such as nordihydroguaiaretic acid (NDGA) (Park S et al. (2004) *J. Cell. Biochem.* 91(5):973-86), CD19 (Chung et al., (2012) *J. Clin. Invest.* 122(6):2257-2266, cohesin (Ewan et al, (2012) *PLoS ONE* 7(11): e 9160), bryostatin 1 (Hu et al. (1993) *Leuk. Lymphoma* 10(1-2): 135-42), 2'-3-dimethyl-4-aminoazobenzene (ortho-aminoazotoluene, OAT) (Smetanina et al. (2011) *Toxicol. Appl. Pharmacol.* 255(1):76-85), 2-amino-1-methyl-6-phenylimidazo[4,5-b]pyridine (PhIP) (Lauber et al. (2004) *Carcinogenesis* 25(12):2509-17), β-estradiol (U.S. Pat. No. 7,544,511 B2), RU38486 (U.S. Pat. No. 7,544,511 B2), dexamethasone (U.S. Pat. No. 7,544,511 B2), thyroid hormones (U.S. Pat. No. 7,544,511 B2), retinoids (U.S. Pat. No. 7,544,511 B2), and ecdysone (U.S. Pat. No. 7,544,511 B2).

Exemplary MYC inhibitors include 7-nitro-N-(2-phenylphenyl)-2,1,3-benzoxadiazol-4-amine (10074-G5) (Clausen D M et al, (2010) *J. Pharmacol. Exp. Ther.* 335(3):715-27), thioxothiazolidinone [Z-]-5-[4-ethylbenzylidene]-2-thioxo-1,3-thiazolidin-4-one (10058-F4) (Clausen et al (2010) *J. Pharmacol. Exp. Ther.* 335(3):715-27; Lin C P et al (2007) *Anticancer Drugs,* 18(2): 161-70; Huang et al (2006) *Exp. Hematol.* 34(11): 1480-9), 4-phenylbutyrate (phenylbutyrate) (Engelhard et al (1998) *J. Neurooncol.* 37(2):97-108), Compound 0012 (Hurley et al (2010) *J. Vasc. Res.* 47(1): 80-90), curcumin (Aggarwal et al (2005) *Clin. Cancer Res.* 1 1(20):7490-8), magnesium hydroxide (Mori et al (1997) *J. Cell. Biochem.* Suppl. 27:35-41), BP-1-102 (Zhang et al (2012) *Proc. Natl. Acad. Sci. U.S.A.* 109(24):9623-8), WP1 193 (Sal et al (2012) *J. Neurooncol.* 107(3):487-501), BP-1-107 (Page et al (2012) *J. Med. Chem.* 55(3): 1047-55), BP-1-108 (Page et al (2012) *J. Med. Chem.* 55(3): 1047-55), SF-1-087 (Page et al (2012) *J. Med. Chem.* 55(3): 1047-55), SF-1-088 (Page et al (2012)

*J. Med. Chem.* 55(3): 1047-55), STX-0119 (Ashizawa et al (2011) *Int. J. Oncol.* 38(5): 1245-52), substituted thiazol-4-one compounds (U.S. Pat. No. 7,872,027), (Z,E)-5-(4-ethylbenzylidene)-2-thioxothiazolidin-4-one (10058-F4) (U.S. Pat. No. 7,026,343), S2T1-60TD (U.S. Publication No. 20120107317A1), Quarfloxin (CX-3543) (U.S. Publication No. 20120107317A1), benzoylanthranilic acid (U.S. Publication No. 20120107317A1), cationic porphyrin TMPyP4 (U.S. Publication No. 20120107317A1), tyrphostin and tryphostin-like compounds (European Patent No. EP2487156A1), AG490 (European Patent No. EP2487156A1), FBXW-7 expression vectors (Ishikawa Y et al, supra), and siRNAs targeting MYC transcript (Id.).

Exemplary NOTCH activators include microRNAs that target FBXW-7 (Ishikawa Y et al supra), AG-370, 5 (U.S. Pat. No. 8,114,422), AG-1296 (6,7-dimethoxy-3-phenylquinoxaline) (Id.), nigericin Na (Id.), cytochalasin D (Id.), FCCP (carbonylcyanide-4-(trifluoromethoxy)-phenylhydrazone) (Id.), SP60012 (Id.), and vectors that produce protein of or isolated protein of Jagged-1, Jagged-2, Jagged-3, Serrate, any member of the Jagged/Serrate protein family, Delta, Delta-like-1, Delta-like-3, Delta-like-4, Delta-like homolog-1 (DLK1), any member of the Delta protein family, and any portion of any of these proteins (PCT Publication WO2004090110A3). Exemplary NOTCH activators may also include chemical activators such as valproic acid (VPA, see, U.S. Pat. No. 8,338,482), resveratrol and phenethyl isothiocyanate.

Exemplary NOTCH inhibitors include gamma-secretase inhibitors such as an arylsulfonamide, a benzodiazepine, L-685,458 (U.S. Patent Publication No. 2001/0305674), MK-0752 (Purow B. (2012) *Adv. Exp. Med. Biol.* 727:305-19; Imbimbo BP (2008) *Curr. Top. Med. Chem.* 8(1):54-61), DAPT ([N-(3,5-Difluorophenacetyl)-L-alanyl]-S-phenylglycine t-butyl ester) (Id.; Ishikawa Y et al. supra; PCT Publication WO2011 149762A3), LY-374973 (N-[N-(3,5-Difluorophenacetyl)-L-alanyl]-S-phenylglycine t-butyl ester) (PCT Publication WO2011 149762A3), N-[(3,5-Difluorophenyl)acetyl]-L-alanyl-2-phenyl]glycine-1,1-dimethylethyl ester (Id.); Lilly GSI L685,458 (Purow B, supra), compound E ((2S)-2-{[(3,5-Difluorophenyl)acetyl] amino}-N-[(3 S)-1-methyl-2-oxo-5-phenyl-2,3-dihydro-1H-1,4-benzodiazepin-3-yl]propanamide) (Purow B, supra), DBZ (dibenzazepine) (Purow B, supra), isocoumarin (Purow B, supra), JLK6 (7-amino-4-chloro-3-methoxyisocoumarin) (Purow B (2012) *Adv. Exp. Med. Biol.* 727:305-19), Compound 18 ([1 1-endo]-N-(5,6,7,8,9,10-hexahydro-6,9-methano benzo[9][8]annulen-11-yl)-thiophene-2-sulfonamide) (Purow B, supra), E2012 (Imbimbo BP, supra; PCT Publication WO2009005688A3), MRK560 (Imbimbo BP, supra), LY-411575 (Imbimbo BP, supra), LY-450139 (Imbimbo BP, supra; PCT Publication WO2009005688A3), γ-secretase inhibitor XII (PCT Publication WO2011 149762A3; PCT Publication WO2009005688A3), 2, 2-dimethyl-N-((S)-6-oxo-6, 7-dihydro-5H-dibenzo(b, d)azepin-7-yl)-N'-(2, 2, 3, 3, 3-pentafluoro-propyl)-malonamide (U.S. Patent Publication No. 20090181944A1), GSI-LX (EP 1949916B1), GSI-X (EP1949916B1), tocopherol derivatives (PCT Publication WO2009040423A1), [(2S)-2-{[(3,5-Difluorophenyl)acetyl]amino}-N-[(3S)l-methyl-2-oxo-5-phenyl-2,3-dihydro-1H-1,4-benzodiazepin-3-yl]propanamide] (PCT Publication WO2009005688A3), N-[N-(3,5-difluorophenacetyl)-L-alanyl]-Sphenylglycine-t-butylester (Id.), [1, l'-Biphenyl]-4-acetic acid (Id.), 2-fluoro-alpha-methyl (Id.), NGX-555 (Id.), LY-41 1575 (Id.) Cellzome (Id.), 2-Thiophenesulfonamide (Id.), 5-chloro-N-[(1S)-3,3,3-trifluoro-1-(hydroxymethyl)-2-(trifluoromethyl) propyl] (Id.), NIC5-15 (Id.), BMS (Id.), CHF-5074 (Id.), BMS-299897 (Imbimbo BP, supra), R04929097; L-685458 ((5S)-(t-Butoxycarbonylamino)-6-phenyl-(4R)hydroxy-(2R)benzylhexanoyl)-L-leu-L-phe-amide); BMS-708163 (Avagacestat); BMS-299897 (2-[(1R)-1-[[(4-Chlorophenyl) sulfonyl](2,5-difluorophenyl)amino]ethyl-5-fluorobenzen-ebutanoic acid); MK-0752; YO-01027; MDL28170 (Sigma); LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-1-alaninamide, see U.S. Pat. No. 6,541,466); ELN-46719 (2-hydroxy-valeric acid amide analog of LY411575 (where LY411575 is the 3,5-difluoromandelic acid amide) (U.S. Pat. No. 6,541,466)); PF-03084014 ((S)-2-((S)-5,7-difluoro-1,2,3,4-tetrahydronaphthalen-3-ylamino)-N-(1-(2-methyl-1-(neopentylamino)propan-2-yl)-1H-imidazol-4-yl)pentanamide, Samon et al., *Mol. Cancer Ther.* 2012; 11: 1565-1575); and Compound E ((2S)-2-{[(3,5-Difluorophenyl)acetyl] amino}-N-[(3S)-1-methyl-2-oxo-5-phenyl-2,3-dihydro-1H-1,4-benzodiazepin-3-yl]propanamide; see WO 98/28268 and Samon et al., *Mol. Cancer Ther.* 2012; 11: 1565-1575; available from Alexis Biochemicals)), or pharmaceutically acceptable salts thereof. In some embodiments, suitable gamma secretase inhibitors include: semagacestat (also known as LY450139, (2S)-2-hydroxy-3-methyl-N-R1S)-1-methyl-2-oxo-2-[[(1S)-2,3,4,5-tetrahydro-3-methyl-2-oxo-1H-3-benzazepin-1-yl] amino] ethylbutanamide, available from Eli Lilly; WO 02/47671 and U.S. Pat. No. 7,468,365); LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-L-alaninamide, available from Eli Lilly, Fauq et al, (2007) *Bioorg. Med. Chem. Lett.* 17: 6392-5); begacestat (also known as GSI-953, U.S. Pat. No. 7,300,951); arylsulfonamides (AS, Fuwa et al, (2006) *Bioorg. Med. Chem. Lett.* 16(16):4184-4189); N-[N-(3,5-difluorophenacetyl)-L-alanyl]-(S)-phenylglycine t-butyl ester (DAPT, Shih et al, (2007) *Cancer Res.* 67: 1879-1882); N-[N-3,5-Difluorophenacetyl]-L-alanyl-S-phenylglycine Methyl Ester (also known as DAPM, gamma-Secretase Inhibitor XVI, available from EMD Millipore); Compound W (3,5-bis(4-Nitrophenoxy)benzoic acid, available from Tocris Bioscience); L-685,458 ((5S)-(tert-Butoxycarbonylamino)-6-phenyl-(4R)-hydroxy-(2R)-benzylhexanoyl)-L-leucy-L-phenylalaninamide, available from Sigma-Aldrich, Shearmen et al, (2000) *Biochemistry* 39, 8698-8704); BMS-289948 (4-chloro-N-(2,5-difluorophenyl)-N-((1 R)-{4-fluoro-2-[3-(1H-imidazol-1-yl)propyl]phenyl}ethyl) benzenesulfonamide hydrochloride, available from Bristol Myers Squibb); BMS-299897 (4-[2-((1R)-{[(4-chlorophenyl)sulfonyl]-2,5-difluoroanilino}ethyl)-5-fluorophenyl]butanoic acid, available from Bristol Myers Squibb, see Zheng et al, (2009) *Xenobiotica* 39(7):544-55); avagacestat (also known as BMS-708163, (R)-2-(4-chloro-N-(2-fluoro-4-(1, 2,4-oxadiazol-3-yl)benzyl)phenylsulfonamido)-5,5,5-trifluoropentanamide, available from Bristol Myers Squibb, Albright et al, (2013) *J Pharmacol. Exp. Ther.* 344(3):686-695); MK-0752 (3-(4-((4-chlorophenyl)sulfonyl)-4-(2,5-difluorophenyl)cyclohexyl)propanoic acid, available from Merck); MRK-003 ((3'R,6R,9R)-5'-(2,2,2-trifluoroethyl)-2-((E)-3-(4-(trifluoromethyl)piperidin-1-yl)prop-1-en-1-yl)-5, 6,7,8,9, 10-hexahydrospiro[6,9-methanobenzo[8]annulene-11,3'-[1,2,5]thiadiazolidine],1'-dioxide, available from Merck, Mizuma et al, (2012) *Mol. Cancer Ther.* 11(9): 1999-2009); MRK-560 (N-[cis-4-[(4-Chlorophenyl)sulfonyl]-4-(2,5-difluorophenyl)cyclohexyl]-1,1,1-trifluoromethanesulfonamide, Best et al, (2006) *J. Pharmacol. Exp. Ther.* 317(2):786-90); RO-4929097 (also known as R4733, (5)-2,2-dimethyl-N1-(6-oxo-6,7-dihydro-5H-dibenzo[b,d]azepin-7-yl)-N3-(2,2,3,3,3-pentafluoropropyl)malonamide, available from Hoffman-La Roche Inc., Tolcher et al, (2012) *J. Clin. Oncol.* 30(19):2348-2353); JLK6 (also known as 7-Amino-4-chloro-3-methoxyisocoumarin, available from Santa Cruz Biotechnology, Inc., Petit et al, (2001) *Nat. Cell. Biol.* 3: 507-511); Tarenflurbil (also known as (R)-Flurbiprofen, (2R)-2-(3-fluoro-4-phenylphenyl)propanoic acid); ALX-260-127 (also known as Compound 11, described by Wolfe et al, (1998) *J. Med. Chem.* 41: 6); Sulindac sulfide (S. Side, et al, (2003) *J. Biol. Chem.* 278(20): 18664-70); 1,1,1-trifluoro-N-(4-[5-fluoro-2-(trifluoromethyl)phenyl]-4-{[4 (trifluoromethyl)phenyl]sulfonyl}cyclohexyl)methanesulfonamide (U.S. Patent Publication No. 20110275719); N-[trans-3-[(4-chlorophenyl)sulfonyl]-3-(2,5-difluorophenyl)cyclobutyl]-1,1,1-trifluoromethanesulfonamide (U.S. Patent Publication No. 20110263580); N-[cis-3-[(4-chlorophenyl)sulfonyl]-3-(2,5-difluorophenyl)cyclobutyl]-1,1,1-trifluoromethanesulfonamide (U.S. Patent Publication No. 20110263580); N-[cis-3-[(4-chlorophenyl)sulfonyl]-3-(2-cyano-5-fluorophenyl)cyclobutyl]-1,1,1-trifluoromethanesulfonamide (U.S. Patent Publication No. 20110263580); N-[cis-3-[(4-chlorophenyl) sulfonyl]-3-(2,5-dichlorophenyl)cyclobutyl]-1,1,1-trifluoromethanesulfonamide (U.S. Patent Publication No. 20110263580); N-(cis-3-(2,5-difluorophenyl)-3-{[4-(trifluoromethyl)phenyl] sulfonyl}cyclobutyl)-1,1,1-trifluoromethanesulfonarnide (U.S. Patent Publication No. 20110263580); N-{cis-3-(5-chloro-2-f luorophenyl)-3-[(4-chlorophenyl)sulfonyl]cyclobutyl}-1,1,1-trifluoromethanesulfonamide (U.S. Patent Publication No. 20110263580); N-{cis-3-(2,5-difluorophenyl)-3-[(4-fluorophenyl)sulfonyl]cyclobutyl}-1,1,1-trifluoromethanesulfonamide (U.S. Patent Publication No. 20110263580); N-{cis-3-(2,5-difluorophenyl)-3-[(3,4-difluorophenyl)sulfonyl]cyclobutyl}-1,1,1-trifluoromethanesulfonamide (U.S. Patent Publication No. 20110263580); N-[cis-3-[(4-cyanophenyl)sulfonyl]-3-(2,5-difluorophenyl)cyclobutyl]-1,1,1-trifluoromethanesulfonamide (U.S. Patent Publication No. 20110263580); 4-{[cis-3-[(4-chlorophenyl)sulfonyl]-3-(2,5-difluorophenyl)cyclobutyl][trifluoromethyl) sulfonyl] amino}butanoic acid (U.S. Patent Publication No. 20110263580); N-[cis-3-[(4-chlorophenyl)sulfonyl]-3-(2,5-difluorophenyl)cyclobutyl]-1, 1,1-trifluoro-N-[2-(tetrahydro-2-pyran-2-yloxy)ethyl]methanesulfonamide (U.S. Patent Publication No. 201 10263580); Methyl{[cis-3-[(4-chlorophenyl)sulfonyl]-3-(2,5-difluorophenyl)cyclobutyl][(trifluoromethyl)sulfonyl]amino}acetate (U.S. Patent Publication No. 201 10263580); N-[3-[(4-chlorophenyl)sulfonyl]-3-(2,5-difluorophenyl)cyclobutyl]-1, 1,1-trifluoro-N-methylmethanesulfonamide (U.S. Patent Publication No. 20110263580); N-[3-[(4-chlorophenyl)sulfonyl]-3-(2,5-difluorophenyl)cyclobutyl]-1, 1, 1-trifluoro-N-methylmethanesulfonamide (U.S. Patent Publication No. 201 10263580); Methyl 4-{[cis-3-[(4-chlorophenyl)sulfonyl]-3-(2,5-difluorophenyl)cyclobutyl] [(trifluoro-methyl)sulfonyl] amino}butanoate (U.S. Patent Publication No. 201 10263580); N-[cis-3-[(4-chlorophenyl)sulfonyl]-3-(2,5-difluorophenyl)cyclobutyl-N-[(trifluoromethyl)sulfonyl]glycine (U.S. Patent Publication No. 20110263580); N-[cis-3-[(4-chlorophenyl)sulfonyl]-3-(2,5-difluorophenyl)-1-methylcyclobutyl]-1, 1,1-trifluoromethanesulfonamide (U.S. Patent Publication No. 20110263580); N-(cis-3-(2,5-difluorophenyl)-1-methyl-3-{[4-(trifluoromethyl)phenyl] sulfonyl}cyclobutyl)-1, 1, 1-trifluoromethanesulfonamide (U.S. Patent Publication No. 20110263580); N-[cis-3-[(4-chlorophenyl)sulfonyl]-3-(2,5-difluorophenyl)cyclobutyl]-1, 1,1-trifluoro-N-[(trifluoromethyl)sulfonyl]methanesulfonamide (U.S. Patent Publication No. 20110263580); Sodium [cis-3-[(4-chlorophenyl)sulfonyl]-3-(2,5-difluorophenyl) cyclobutyl] [(trifluoromethyl)sulfonyl]azanide (U.S. Patent Publication No. 201 10263580); Potassium[cis-3-[(4-chlorophenyl)sulfonyl]-3-(2,5-difluorophenyl)cyclo butyl] [(trifluoromethyl)sulfonyl]azanide (U.S. Patent Publication No. 201 10263580); N-[cis-3-[(4-trifluoromethoxyphenyl)sulfonyl]-3-(2,5-difluorophenyl)cyclobutyl]-1, 1, 1-trifluoromethanesulfonamide (U.S. Patent Publication No. 201 10263580); 1, 1, 1-trifluoro-N-(4-[5-fluoro-2-(trifluoromethyl)phenyl]-4-{[4-(trifluoromethyl)phenyl]sulfonyl}cyclohexyl)methanesulfonamide (U.S. Patent Publication No. 201 10263580); gamma-Secretase Inhibitor I (also known as Z-Leu-Leu-Nle-CHO, benzyloxycarbonyl-leucyl-leucyl-norleucinal, available from Calbiochem); gamma-secretase inhibitor II: (MOL)(CDX) (available from Calbiochem); gamma secretase inhibitor III, (N-Benzyloxycarbonyl-Leu-leucinal, available from Calbiochem); gamma secretase inhibitor IV, (N-(2-Naphthoyl)-Val-phenylalaninal, available from Calbiochem); gamma-secretase inhibitor V (also known as Z-LF-CHO, N-Benzyloxycarbonyl-Leu-phenylalaninal, available from EMD Millipore); gamma-secretase inhibitor VI (1-(S)-endo-N-(1,3,3)-Trimethylbicyclo[2.2.1]hept-2-yl)-4-fluorophenyl Sulfonamide, available from EMD Millipore); gamma secretase inhibitor VII, (also known as Compound A, MOC-LL-CHO, Menthyloxycarbonyl-LL-CHO, available from Calbiochem); gamma secretase inhibitor X, ({1S-Benzyl-4R-[1-(1S-carbamoyl-2-phenethylcarbamoyl)-1S-3-methylbutylcarbamoyl]-2R-hydroxy-5-phenylpentyl}carbamic acid tert-butyl ester, available from Calbiochem); gamma secretase inhibitor XI, (7-Amino-4-chloro-3-methoxyisocoumarin, available from Calbiochem); gamma secretase inhibitor XII, (also known as Z-Ile-Leu-CHO, Shih and Wang, (2007) *Cancer Res.* 67: 1879-1882); gamma secretase inhibitor XIII, (Z-Tyr-Ile-Leu-CHO, available from Calbiochem); gamma secretase inhibitor XIV, (Z-Cys(t-Bu)-Ile-Leu-CHO, available from Calbiochem); gamma secretase inhibitor XVII, (also known as WPE-III-31C), (MOL)(CDX) (available from Calbiochem); gamma secretase inhibitor XIX, (also known as benzodiazepine, (2S,3R)-3-(3,4 Difluorophenyl)-2-(4-fluorophenyl)-4-hydroxy-N-((3S)-2-oxo-5-phenyl-2,3-dihydro-1H-benzo[e][1,4]diazepin-3-yl)-butyramide, Churcher et al, (2003) *J. Med. Chem.* 46(12):2275-8); gamma secretase inhibitor XX, (also known as dibenzazepine, (S,S)-2-[2-(3, 5-Difluorophenyl)acetylamino]-N-(5-methyl-6-oxo-6,7-dihydro-5H-dibenzo[b,d]azepin-7-yl)propionamide, (MOL)(CDX) (Weihofen et al, Science 296: 2215-2218, 2002, available from Calbiochem); gamma secretase inhibitor XXI, ((S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide, available from Calbiochem); 5-methyl-2-propan-2-ylcyclohexyl)N-[4-methyl-1-[(4-methyl-1-oxopentan-2-yl)amino]-1-oxopentan-2-yl]carbamate (available from HDH Pharma Inc.); N-trans-3,5-Dimethoxycinnamoyl-Ile-leucinal (available from Calbiochem); N-tert-Butyloxycarbonyl-Gly-Val-Valinal; isovaleryl-V V-Sta-A-Sta-OCH$_3$ (available from Calbiochem); diethyl-(5-phenyl-3H-azepin-2-yl)-amine (U.S. Pat. No. 8,188,069); diethyl-(5-isopropyl-3H-azepin-2-yl)-amine (Patent No. 8188069); diethyl-(4-phenyl-3H-azepin-2-yl)-amine (U.S. Pat. No. 8,188,069); diethyl-(6-phenyl-3H-azepin-2-yl)-amine (U.S. Pat. No. 8,188,069); 5-phenyl-1,3-dihydro-azepin-2-one (U.S. Pat. No. 8,188,069); -Isopropyl-1,3-dihydro-azepin-2-one (U.S. Pat. No. 8,188, 069); 4-phenyl-1,3-dihydro-azepin-2-one (U.S. Pat. No. 8,188,069); 6-phenyl-1,3-dihydro-azepin-2-one (U.S. Pat.

No. 8,188,069); 2-butoxy-5-phenyl-3H-azepine (U.S. Pat. No. 8,188,069); 1-methyl-5-phenyl-1,3-dihydro-azepin-2-one (U.S. Pat. No. 8,188,069); 5-isopropyl-1-methyl-1,3-dihydro-azepin-2-one (U.S. Pat. No. 8,188,069); 1-methyl-4-phenyl-1,3-dihydro-azepin-2-one (U.S. Pat. No. 8,188,069); 1-methyl-6-phenyl-1,3-dihydro-azepin-2-one (U.S. Pat. No. 8,188,069); 1-methyl-5-phenyl-1H-azepine-2,3-dione-3-oxime (U.S. Pat. No. 8,188,069); 5-isopropyl-1-methyl-1H-azepine-2,3-dione-3-oxime (U.S. Pat. No. 8,188,069); 1-methyl-6-phenyl-1H-azepine-2,3-dione-3-oxime (U.S. Pat. No. 8,188,069); 1-methyl-4-phenyl-1H-azepine-2,3-dione-3-oxime (U.S. Pat. No. 8,188,069); 3-amino-1-methyl-5-phenyl-1,3-dihydro-azepin-2-one (U.S. Pat. No. 8,188,069); 3-amino-5-isopropyl-1-methyl-1,3-dihydro-azepin-2-one (U.S. Pat. No. 8,188,069); 3-amino-1-methyl-4-phenyl-1,3-dihydro-azepin-2-one (U.S. Pat. No. 8,188,069); 3-amino-1-methyl-6-phenyl-1,3-dihydro-azepin-2-one (U.S. Pat. No. 8,188,069); (S)-[1-(1-methyl-2-oxo-5-phenyl-2,3-dihydro-1H-azepin-3-ylcarbamoyl)-ethyl]-carbamic acid tertbutyl ester (U.S. Pat. No. 8,188,069); [(S)-1-(5-isopropyl-1-methyl-2-oxo-2,3-dihydro-1H-azepin-3-ylcarbamoyl)-ethyl]carbamic acid tert-butyl ester (U.S. Pat. No. 8,188,069); [(5)-1-(1-methyl-2-oxo-4-phenyl-2,3-dihydro-1H-azepin-3-ylcarbamoyl)-ethyl]carbamic acid tert-butyl ester (U.S. Pat. No. 8,188,069); [(S)-1-(1-methyl-2-oxo-6-phenyl-2,3-dihydro-1H-azepin-3-ylcarbamoyl)-ethyl]-carbamic acid tert-butyl ester (U.S. Pat. No. 8,188,069); (S)-2-amino-N-(1-methyl-2-oxo-5-phenyl-2,3-dihydro-1H-azepin-3-yl)-propionamide (U.S. Pat. No. 8,188,069); (S)-2-amino-N-(5-isopropyl-1-methyl-2-oxo-2,3-dihydro-1H-azepin-3-yl)propionarnide (U.S. Pat. No. 8,188,069); (S)-2-Amino-N-(l-methyl-2-oxo-6-phenyl-2,3-dihydro-1H-azepin-3-yl)propionamide hydrochloride (U.S. Pat. No. 8,188,069); (S)-2-Amino-N-(l-methyl-2-oxo-4-phenyl-2,3-dihydro-1H-azepin-3-yl) propionamide hydrochloride (U.S. Pat. No. 8,188,069); (S)-2-fluoro-3-methyl-butyric acid (U.S. Pat. No. 8,188,069); (S)-2-hydroxy-3-methyl-N-[(S)-1-((S)-1-methyl-2-oxo-5-phenyl-2,3-dihydro-1H-azepin-3-ylcarbamoyl)-ethyl]-butyramide (U.S. Pat. No. 8,188,069); (S)-2-fluoro-3-methyl-N-[(S)-1-(1-methyl-2-oxo-5-phenyl-2,3-dihydro-1H-azepin-3-ylcarbamoyl)-ethyl]-butyramide (U.S. Pat. No. 8,188,069); (5)-2-hydroxy-N-[(S)-1-(5-isopropyl-1-methyl-2-oxo-2,3-dihydro-1H-azepin-3-ylcarbamoyl)ethyl]-3-methyl-butyramide (U.S. Pat. No. 8,188,069); (5)-2-hydroxy-3-methyl-N-[(S)-1-(1-methyl-2-oxo-4-phenyl-2,3-dihydro-1H-azepin-3-ylcarbamoyl)-ethyl]-butyramide (U.S. Pat. No. 8,188,069); (S)-2-hydroxy-3-methyl-N-[(S)-1-(1-methyl-2-oxo-6-phenyl-2,3-dihydro-1H-azepin-3-ylcarbamoyl)-ethyl]-butyramide (U.S. Pat. No. 8,188,069); and(S)-2-fluoro-3-methyl-N-[(S)-1-(1-methyl-2-oxo-6-phenyl-2,3-dihydro-1H-azepin-3-ylcarbamoyl)-ethyl]-butyramide (U.S. Pat. No. 8,188,069), and pharmaceutically acceptable salts thereof.

Additional exemplary NOTCH inhibitors include non-steroidal anti-inflammatory drugs (NSAIDs) such as flurbiprofen (Purow B, supra), MPC-7869 (Imbimbo BP, supra), ibuprofen (Id.), sulindac sulphide, indomethacin, alpha-secretase inhibitors (ASIs) (Purow B, supra), the $Na^+/H^+$ antiporter Monensin (Id.); small molecules that block NOTCH binding to interacting proteins such as Jagged, Numb, Numb-like, CBF1 transcription factor, and mastermind-like (MAML) (Id.; Ishikawa Y et al, supra.); antibodies that bind NOTCH proteins or NOTCH ligands such as Delta-Like-4 (Purow B, supra); stapled peptides that bind NOTCH such as SAHM1 (Id.); dominant-negative forms of genes such as MAML (Id; Ishikawa Y et al., supra), Numb/Numb-Like (Purow B, supra), and FBXW-7 (Id.); expression vectors that increase levels of NOTCH regulators such as FBXW-7 (Id.; Ishikawa Y et al., supra); siRNAs that target NOTCH transcripts (Purow B, supra); microRNAs such as miR-326, miR-34a, microRNA-206, and miR-124 (Id.); and NOTCH antibodies (U.S. Pat. No. 8,226,943, U.S. Publication No. 20090258026A2, PCT Publication WO2012080926A2).

Exemplary Atoh1 activators include, for example, β-Catenin or β-catenin pathway agonists, e.g., Wnt ligands, DSH/DVL1, 2, 3, LRP65N, WNT3A, WNTSA, and WNT3A, 5A. Additional Wnt/β-catenin pathway activators and inhibitors are reviewed in the art (Moon et al, *Nature Reviews Genetics,* 5:689-699, 2004). In some embodiments, suitable Wnt/-catenin pathway agonists can include antibodies and antigen binding fragments thereof, and peptides that bind specifically to frizzled (Fzd) family of receptors.

Kinase inhibitors, e.g., casein kinase 1 (CK1) and glycogen synthase kinase 3 β (GSK3) inhibitors can also act as β-Catenin or β-catenin pathway agonists to activate Atoh1. GSK3 β inhibitors include, but are not limited to, lithium chloride (LiCl), Purvalanol A, olomoucine, alsterpaullone, kenpaullone, benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-dibenzyl-5-oxothiadiazolidine-3-thione (OTDZT), (27,3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-ethanone, N-(4-Methoxybenzyl)-N'-(5-nitro-1,3-thiazol-2-yl)urea (AR-A014418), and indirubins (e.g., indirubin-5-sulfonamide; indirubin-5-sulfonic acid (2-hydroxyethyl)-amide indirubin-3'-monoxime; 5-iodo-indirubin-3'-monoxime; 5-fluoroindirubin; 5,5'-dibromoindirubin; 5-nitroindirubin; 5-chloroindirubin; 5-methylindirubin, 5-bromoindirubin), 4-Benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-Dibenzyl-5-oxothiadiazolidine-3-thione (OTDZT), (27,3'E)-6-Bromoindirubin-3'-oxime (BIO), a-4-Dibromo-acetophenone (i.e., Tau Protein Kinase I (TPK I) Inhibitor), 2-Chloro-1-(4,5-dibromo-thiophen-2-yl)-ethanone, (vi) N-(4-Methoxybenzyl)-N'-(5-nitro-1,3-thiazol-2-yl)urea (AR-A014418), and H-KEAPPAPPQSpP-$NH_2$ (L803) or its cell-permeable derivative Myr-N-GKEAPPAPPQSpP-$NH_2$ (L803-mts). Other GSK3β inhibitors are disclosed in U.S. Pat. Nos. 6,417,185; 6,489,344; and 6,608,063. In some embodiments, suitable kinase inhibitors can include RNAi and siRNA designed to decrease GSK3β and/or CK1 protein levels. In some embodiments, useful kinase inhibitors include FGF pathway inhibitors. In some embodiments, FGF pathway inhibitors include, for example, SU5402.

Additional Atoh1 activators include gamma secretase inhibitors (e.g., arylsulfonamides, dibenzazepines, benzodiazepines, N-[N-(3,5-difluorophenacetyl)-L-alanyl]-(S)-phenylglycine t-butyl ester (DAPT; EMD Biosciences, San Diego, Calif., USA), L-685,458, or MK0752ho, in addition to those listed above under NOTCH inhibitors), gentaMY- Cin, and the combination of transcription factors Eyal and Sixl (and optionally Sox2), as described in Ahmed et al (2012) *Dev. Cell.* 22(2):377-390.

Additional Atoh1 activators are described in U.S. Pat. No. 8,188,131, including a compound represented by Formula I:

A.

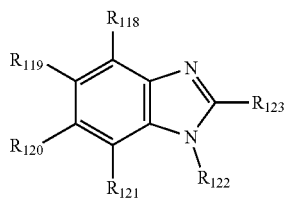

(I)

wherein:

each of $R_{118}$, $R_{119}$, $R_{120}$, and $R_{121}$ is, independently selected from H, halo, OH, CN, $NO_2$, $C_1$-$C_3$ alkyl, $C_1$-$C_3$ haloalkyl, alkoxy, and $C_1$-$C_8$ haloalkoxy;

$R_{122}$ is hydrogen or —Z—$R^a$; wherein:

Z is O or a bond; and $R^a$ is:

(i) $C_1$-$C_6$ alkyl or $C_1$-$C_6$ haloalkyl, each of which is optionally substituted with from 1-3 $R^b$; or (ii) $C_3$-$C_{10}$ cycloalkyl, $C_3$-$C_{10}$ cycloalkenyl, each of which is optionally substituted with from 1-5 $R^c$; or (iii) $C_7$-$C_{11}$ aralkyl, or heteroaralkyl including 6-11 atoms, each of which is optionally substituted with from 1-5 $R^c$;

(iv) $C_6$-$C_{10}$ aryl or heteroaryl including 5-10 atoms, each of which is optionally substituted with from 1-5 $R^d$;

$R_{123}$ is:

(i) hydrogen; or (ii) $C_1$-$C_6$ alkyl or $C_1$-$C_6$ haloalkyl, each of which is optionally substituted with from 1-3 $R^b$; or (iii) $C_6$-$C_{10}$ aryl or heteroaryl including 5-10 atoms, each of which is optionally substituted with from 1-5 $R^d$; or (iv) $C_7$-$C_{11}$ aralkyl, or heteroaralkyl including 6-11 atoms, each of which is optionally substituted with from 1-5 $R^c$; or (v) —($C_1$-$C_6$ alky-$Z^1$—($C_6$-$C_{10}$ aryl), wherein $Z^1$ is O, S, NH, or N($CH_3$); the alkyl portion is optionally substituted with from 1-3 $R^b$; and the aryl portion is optionally substituted with from 1-5 $R^d$; or (vi) —($C_1$-$C_6$ alkyl)-$Z^2$-(heteroaryl including 5-10 atoms), wherein $Z^2$ is O, S, NH, or N($CH_3$); the alkyl portion is optionally substituted with from 1-3 $R^b$; and the heteroaryl portion is optionally substituted with from 1-5 $R^d$; or (vii) —($C_1$-$C_6$ alkyl)-$Z^3$—($C_3$-$C_{10}$ cycloalkyl), wherein $Z^3$ is O, S, NH, or N($CH_3$); the alkyl portion is optionally substituted with from 1-3 $R^b$; and the cycloalkyl portion is optionally substituted with from 1-5 $R^c$; $R^b$ at each occurrence is, independently:

(i) $NH_2$; NH($C_1$-$C_3$ alkyl); N($C_1$-$C_3$ alkyl)$_2$; hydroxy; $C_1$-$C_6$ alkoxy or $C_1$-$C_6$ haloalkoxy; or (ii) $C_3$-$C_7$ cycloalkyl optionally substituted with from 1-3 substituents independently selected from $C_1$-$C_6$ alkyl, $NH_2$; NH($C_1$-$C_3$ alkyl); N($C_1$-$C_3$ alkyl)$_2$; hydroxy; $C_1$-$C_6$ alkoxy or $C_1$-$C_6$ haloalkoxy;

$R^c$ at each occurrence is, independently:

(i) halo; $NH_2$; NH($C_1$-$C_3$ alkyl); N($C_1$-$C_3$ alkyl)$_2$; hydroxy; $C_1$-$C_6$ alkoxy; $C_1$-$C_6$ haloalkoxy; or oxo; or (ii) $C_1$-$C_6$ alkyl or $C_1$-$C_6$ haloalkyl; and $R^d$ at each occurrence is, independently:

(i) halo; $NH_2$; NH($C_1$-$C_3$ alkyl); N($C_1$-$C_3$ alkyl)$_2$; hydroxy; $C_1$-$C_6$ alkoxy or $C_1$-$C_6$ haloalkoxy; nitro; —NHC (O)($C_1$-$C_3$ alkyl); or cyano; or (ii) $C_1$-$C_6$ alkyl or $C_1$-$C_6$ haloalkyl; or a pharmaceutically acceptable salt thereof.

Other exemplary Atoh1 activators described in U.S. Pat. No. 8,188,131 include 4-(4-chlorophenyl)-1-(5H-pyrimido [5,4-b] indol-4-yl)-1H-pyrazol-3-amine; 6-chloro-1-(2-chlorobenzyloxy)-2-phenyl-1H-benzo[d]imidazole; 6-chloro-1-(2-chlorobenzyloxy)-2-(4-methoxyphenyl)-1H-benzo[d] imidazole; 6-chloro-2-(4-methoxyphenyl)-1-(4-methylbenzyloxy)-1H-benzo[d] imidazole; 6-chloro-1-(3,5-dimethylbenzyloxy)-2-(4-methoxyphenyl)-1H-benzo [d] imidazole; 6-chloro-1-(4-methoxybenzyloxy)-2-(4-methoxyphenyl)-1H-benzo [d] imidazole; 1-(4-methylbenzyloxy)-6-nitro-2-phenyl-1H-benzo[d] imidazole; 4-(1H-benzo[d] imidazol-2-yl)phenol; 2,5-dichloro-N-((1-methyl-1H-benzo[d]imidazol-2-yl)methyl)aniline; 4-(2-(1-methyl-1H-benzo[d]imidazol-2-yl)ethyl)aniline; 2-((2-methoxyphenoxy)methyl)-1H-benzo[d]imidazole; 2-((4-fluorophenoxy)methyl)-1-methyl-1H-benzo [d] imidazole; 2-(phenylthiomethyl)-1H-benzo [d] imidazole; 3-(6-methyl-1H-benzo[d]imidazole-2-yl)-2H-chromen-2-imine; N-(2-(1H-benzo[d]imidazole-2-yl)phenyl)isobutyramide; 2-(o-tolyloxymethyl)-1H-benzo[d]imidazole; 2-(4-methoxyphenyl)-1-phenethyl-1H-benzo[d]imidazole; N-(6-bromobenzo[d]thiazole-2-yl)thiophene-2-carboxamide; N-(benzo[d]thiazole-2-yl)-1-methyl-1H-pyrazole-5-carboxamide; 2-(4-fluorobenzylthio)benzo[d]thiazole; 5-chloro-N-methylbenzo[d]thiazole-2-amine; N-(6-acetamidobenzo[d] thiazol-2-yl)furan-2-carboxamide; N-(6-fluorobenzo[d] thiazole-2-yl)-3-methoxybenzamide; 2-(benzo[d]oxazol-2-ylthio)-N-(2-chlorophenyl)acetamide; 5-chloro-2-phenylbenzo[d]oxazole; 5-methyl-2-m-tolylbenzo[d] oxazole; 2-(4-isobutoxyphenyl)-3-(naphthalen-2-yl)-2,3-dihydroquinazolin-4(1H)-one; N-(2-(2-(4-fluorophenyl)-2-oxoethylthio)-4-oxoquinazolin-3(4H)-yl)benzamide; 2-(4-chlorophenyl)-4-(4-methoxyphenyl)-1,4-dihydrobenzo[4,5] imidazo [1,2-a]pyrimidine; 2-(3-pyridyl)-4-(4-bromophenyl)-1,4-dihydrobenzo[4,5]imidazo [1,2-a] pyrimidine; N-sec-butyl-1,7,7-trimethyl-9-oxo-8,9-dihydro-7H-furo[3,2-f]chromene-2-carboxamide; N-(3-carbamoyl-5,6-dihydro-4H-cyclopenta[b]thiophen-2-yl)benzofuran-2-carboxamide; 3-chloro-N-(5-chloropyridin-2-yl)benzo[b] thiophene-2-carboxamide; 3-chloro-N-((tetrahydrofuran-2-yl)methyl)benzo[b]thiophene-2-carboxamide; N-(3-(5-chloro-3-methylbenzo[b]thiopen-2-yl)-1H-pyrazol-5-yl) acetamide; 2-(naphthalen-2-yl)-1H-indole; 2-(pyridin-2-yl)-1H-indole; N-(2-chlorophenyl)-2-(1H-indole-3-yl)-2-oxoacetamide; 2-m-tolylquinoline; 2-(4-(2-methoxyphenyl) piperazin-1-yl)quinolone; 2-(1H-benzo[d][1,2,3]triazol-1-yl)-N-(2,3-dihy dro-1H-inden-2-yl)acetamide; 1-phenethyl-1H-benzo[d] [1,2,3]triazole; 7-(4-fluorobenzyloxy)-2H-chromen-2-one; N-(2,4-dichlorophenyl)-8-methoxy-2H-chromene-3-carboxamide; N-(3-chlorophenyl)-8-methyl-3,4-dihydroquinoline-1(2H)-carbothioamide; 7-methoxy-5-methyl-2-phenyl-4H-chromen-4-one; 2-(3,4-dimethylphenyl)quinoxaline; 4-bromo-N-(5-chloropyridin-2-yl)benzamide; 3-amino-6,7,8,9-tetrahydro-5H-cyclohepta [e]thieno[2,3-b]pyridine-2-carboxamide; (Z)-3-methyl-N'-(nicotinoyloxy)benzimidamide; N,N-diethyl-6-methoxythieno[2,3-b]quinoline-2-carboxamide; 6-(4-methoxyphenyl)-1,2,3,4-tetrahydro-1,5-naphthyridine; 5-bromo-N-(2-(phenylthio)ethyl) nicotinamide; N-(6-methylpyridin-2-yl)-2,3-dihydrobenzo[b][1,4]dioxine-6-carboxamide; 2-(4-methylbenzylthio)oxazolo [4,5-b]pyridine; N-(2-methoxyethyl)-5-p-tolylpyrimidin-2-amine; 4-(5-

(benzo[b]thiophen-2-yl)pyrimidin-2-yl)morpholino; 4-(5-(4-fluorophenyl)pyrimidin-2-yl)morpholino; N-(4-bromo-3-methylphenyl)quinazoline-4-amine; N-(4-methoxyphenyl)quinazolin-4-amine; N-(3-methoxyphenyl)-9H-purin-6-amine; N,N-diethyl-1-m-tolyl-1H-pyrazolo [3,4-d] pyrimidin-4-amine; (5-(4-bromophenyl)furan-2-yl)(morpholino)methanone; (Z)-4-bromo-N'-(furan-2-carbonyloxy) benzimidamide; N-(4-iodophenyl)furan-2-carboxamide; 5-(5-(2,4-difluorophenyl)furan-2-yl)-1-(methylsulfonyl)-1H-pyrazole; 1-(3-amino-5-(4-tert-butylphenyl)thiophen-2-yl)ethanone; N-(3-cayano-4,5,6,7-tetrahydrobenzo[b]thiophen-2-yl)-2-fluorobenzamide; N-(5-chloropyridin-2-yl) thiophene-2-carboxamide; N-(2-(4-fluorophenoxy)ethyl) thiophene-2-carboxamide; 2,5-dimethyl-N-phenyl-1-(thiophen-2-ylmethyl)-1H-pyrrole-3-carboxamide; N-(3-cyanothiophen-2-yl)-4-isopropoxybenzamide; 2-(4-methoxyphenoxy)-N-(thiazol-2-yl)acetamide; 4-(4-methoxyphenyl)-N-(3-methylpyridin-2-yl)thiazol-2-amine; 4-(biphenyl-4-yl)thiazol-2-amine; 4-(4-(4-methoxyphenyl) thiazol-2-yl)-3-methylisoxazol-5-amine; N-(2-methoxyphenyl)-4-phenylthiazol-2-amine; 1-(4-amino-2-(m-tolylamino) thiazol-5-yl)-2-methylpropan-1-one; 4-(4-chlorophenyl)-1-(5H-pyrimido[5,4-b]indol-4-yl)-1H-pyrazol-3-amine; 2-(4-chlorophenyl)-6-ethyl-5-methylpyrazolo[1,5-a]pyrimidin-7 (4H)-one; 5-methoxy-2-(5-phenyl-1H-pyrazol-3-yl)phenol; (3-(4-bromophenyl)-1-phenyl-1H-pyrazol-4-yl)methanol; N-(2,5-dichlorophenyl)-1-ethyl-1H-pyrazole-3-carboxamide; 4-chloro-1-methyl-N-(2-oxo-2-phenylethyl)-1H-pyrazole-3-carboxamide; N-(3-(5-tert-butyl-2-methylfuran-3-yl)-1H-pyrazole-5-yl)benzamide; N-(5-methylisoxazol-3-yl)benzo [d] [1,3]dioxole-5-carboxamide; (5-(4-bromophenyl)isoxazole-3-yl)(morpholino)methanone; N-(4-bromophenyl)-5-isopropylisoxazole-3-carboxamide; 5-((4-chloro-2-methylphenoxy)methyl)-3-(pyridin-4-yl)-1, 2,4-oxadiazole; 5-(2-methoxyphenyl)-3-p-tolyl-1,2,4-oxadiazole; 5-(phenoxymethyl)-3-(pyridin-3-yl)-1,2,4-oxadiazole; 5-(2-chloro-4-methylphenyl)-3-(pyridin-3-yl)-1,2,4-oxadiazole; 3-(2-chlorophenyl)-5-p-tolyl-1,2,4-oxadiazole; 5-(piperidin-1-ylmethyl)-3-p-toyl-1,2,4-oxadiazole; 5-(4-bromophenyl)-3-(pyridin-3-yl)-1,2,4-oxadiazole; 5-(2-bromophenyl)-3-(4-bromophenyl)-1,2,4-oxadiazole; 5-(2-bromo-5-methoxyphenyl)-3-(thiophenyl-2-yl)-1,2,4-oxadiazole; 3-(2-fluorophenyl)-N-(3-(piperidin-1-yl) propyl)-1,2,4-oxadiazol-5-amine; 2-(2-chlorobenzoyl)-N-(4-fluorophenyl)hydrazinecarbothioamide; 2-(methylamino)-N-phenethylbenzamide; 4-tert-butyl-N-((tetrahydrofuran-2-yl)methyl)benzamide; 2-phenyl-5-o-tolyl-1,3,4-oxadiazole; 4-(3-(4-chlorophenyl)-4,5-dihydro-1H-1,2,4-triazole-5-yl)-N,N-dimethylaniline; 7-methoxy-2-(4-methoxyphenyl)-1, 10b-dihydrospiro[benzo[e]pyrazolo[1, 5-c] [1,3]oxazine-5, 1'-cyclohexane]; 6-oxo-2-(4-(3-(trifluoromethyl)phenoxy)phenyl)-1,4,5,6-tetrahydropyridine-3-carbonitrile; 6-(4-methoxyphenyl)imidazo[2, 1-b] thiazole; 2-(2-bromophenoxy)-N-(4H-1,2,4-triazol-3-yl)acetamide; 1-(indolin-1-yl)-2-phenoxyethanone; 2-(4-chlorophenyl)-6,7,8,9-tetrahydrobenzo[e]imidazo [1,2-b][1,2,4] triazine; and pharmaceutically acceptable salts thereof.

Delivery of Agents for Modulating mTOR, PTEN, MYC, NOTCH and Atoh1: The method of delivery of modulators of mTOR, PTEN, MYC, NOTCH or Atoh1 expression or activity will depend, in part, upon whether the hair cells or supporting cells are being contacted with the agents of interest in vivo or ex vivo. In the in vivo approach, the agents are delivered into the inner ear of a mammal. In the ex vivo approach, cells are contacted with the agents ex vivo. The resulting hair cells can then be transplanted into the inner ear of a recipient using techniques known and used in the art.

In certain embodiments, the mTOR activator is administered such that the mTOR activity or expression is increased by 5%, 10%, 15%, 20%, 25%, 30%, 40%, 50%, 60%, 70%, 75%, 80%, 85%, 90%, 95%, 96%, 97%, 98%, 99% or 100% as compared to a baseline control.

In certain embodiments, the mTOR expression or activity is increased by administering an mTOR activator in the inner ear of a recipient to give, for example, a final concentration of greater than about 30 µM, for example, in the range of about 30 µM to about 1000 µM. In certain embodiments, the mTOR activator can be administered in an amount sufficient to give a final concentration of greater than about 30 µM. For example, the mTOR activator may be administered in an amount sufficient to give a final concentration in the range from about 30 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM.

In other embodiments, mTOR activator is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the mTOR activator can be administered locally to the inner ear of a mammal. In one embodiment, 0.5 mg the mTOR activator is administered locally to the inner ear. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of mTOR activator can be administered locally to the inner ear of a mammal.

In certain embodiments, the PTEN inhibitor is administered such that PTEN activity or expression is decreased by 5%, 10%, 15%, 20%, 25%, 30%, 40%, 50%, 60%, 70%, 75%, 80%, 85%, 90%, 95%, 96%, 97%, 98%, 99% or 100% as compared to a baseline control.

In certain embodiments, the PTEN expression or activity is decreased by administering a PTEN inhibitor in the inner ear of a recipient to give, for example, a final concentration of greater than about 30 µM, for example, in the range of about 30 µM to about 1000 µM. In certain embodiments, the mTOR activator can be administered in an amount sufficient to give a final concentration of greater than about 30 µM. For example, the PTEN inhibitor may be administered in an amount sufficient to give a final concentration in the range from about 30 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM.

In other embodiments, the PTEN inhibitor is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the PTEN inhibitor can be administered locally to the inner ear of a mammal. In one embodiment, 0.5 mg the PTEN inhibitor is administered locally to the inner ear. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of PTEN inhibitor can be administered locally to the inner ear of a mammal.

In certain embodiments, the MYC activator is administered such that the MYC activity or expression is increased by 5%, 10%, 15%, 20%, 25%, 30%, 40%, 50%, 60%, 70%, 75%, 80%, 85%, 90%, 95%, 96%, 97%, 98%, 99% or 100% as compared to a baseline control.

In certain embodiments, MYC activity or expression is increased by administering MYC protein or a MYC activator in the inner ear of a recipient to give, for example, a final concentration of greater than about 30 µM, for example, in the range of about 30 µM to about 1000 µM. In certain embodiments, the MYC protein or MYC activator can be administered in an amount sufficient to give a final concentration of greater than about 30 µM. For example, the MYC protein or MYC activator may be administered in an amount sufficient to give a final concentration in the range from about 30 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM.

In other embodiments, MYC protein or a MYC activator is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the MYC protein or MYC activator can be administered locally to the inner ear of a mammal. In one embodiment, 0.5 mg of MYC protein or MYC activator is administered locally to the inner ear. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of MYC protein or MYC activator can be administered locally to the inner ear of a mammal.

In certain embodiments, the NOTCH activator is administered such that the NOTCH activity or expression is increased by 5%, 10%, 15%, 20%, 25%, 30%, 40%, 50%, 60%, 70%, 75%, 80%, 85%, 90%, 95%, 96%, 97%, 98%, 99% or 100% as compared to a baseline control.

In certain embodiments, NOTCH activity or expression is increased by administering a NOTCH protein, a NICD protein or a NOTCH activator to an inner ear of a recipient to give a final concentration of greater than about 30 µM, for example, in the range of about 30 µM to about 1000 µM. In certain embodiments, a NOTCH protein, NICD protein or NOTCH activator can be administered in an amount sufficient to give a final concentration of greater than about 30 µM. For example, the NOTCH protein, NICD protein or NOTCH activator may be administered in an amount sufficient to give a final concentration in the range from about 30 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM.

In other embodiments, NOTCH protein, NICD protein or NOTCH activator is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the NOTCH protein, NICD protein or NOTCH activator can be administered locally to the inner ear of a mammal. In one embodiment, 0.5 mg of NOTCH protein, NICD protein or NOTCH activator is administered locally to the inner ear of a mammal. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of NOTCH protein, NICD protein or NOTCH activator can be administered locally to the inner ear of a mammal.

In certain embodiments, after cell proliferation has occurred, NOTCH activity is inhibited by administering a NOTCH inhibitor. A NOTCH inhibitor can be administered to give a final concentration of greater than about 30 µM, for example, in the range of about 30 µM to about 1000 µM. In certain embodiments, a NOTCH inhibitor can be administered in an amount sufficient to give a final concentration of greater than about 30 µM. For example, the NOTCH inhibitor may be administered in an amount sufficient to give a final concentration in the range from about 30 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM. In certain embodiments, the NOTCH inhibitor is administered in an amount sufficient to give a final concentration of about 400 µM.

In other embodiments, a NOTCH inhibitor is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the NOTCH inhibitor can be administered locally to the inner ear of a mammal. In one embodiment, 0.5 mg of NOTCH inhibitor is administered locally to the inner ear of a mammal. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of NOTCH inhibitor can be administered locally to the inner ear of a mammal. In certain embodiments, about 0.7 mg NOTCH inhibitor is administered locally to the inner ear of a mammal.

In certain embodiments, the Atoh1 activator is administered such that the Atoh1 activity or expression is increased by 5%, 10%, 15%, 20%, 25%, 30%, 40%, 50%, 60%, 70%, 75%, 80%, 85%, 90%, 95%, 96%, 97%, 98%, 99% or 100% as compared to a baseline control.

In certain embodiments, Atoh1 activity or expression is increased by administering Atoh1 protein or an Atoh1 activator in the inner ear of a recipient to give, for example, a final concentration of greater than about 30 µM, for example, in the range of about 30 µM to about 1000 µM. In certain embodiments, the Atoh1 protein or Atoh1 activator can be administered in an amount sufficient to give a final concentration of greater than about 30 µM. For example, the Atoh1 protein or Atoh1 activator may be administered in an amount sufficient to give a final concentration in the range from about 30 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM.

In other embodiments, Atoh1 protein or a Atoh1 activator is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the Atoh1 protein or Atoh1 activator can be administered locally to the inner ear of a mammal. In one embodiment, 0.5 mg of Atoh1 protein or Atoh1 activator is administered locally to the inner ear. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of Atoh1 protein or Atoh1 activator can be administered locally to the inner ear of a mammal.

Alternative Methods for Delivery of DNA

In some aspects, the activity or expression of mTOR, MYC, NOTCH or Atoh1 can be increased in a target cell and PTEN activity or expression can be decreased in a target cell using expression constructs known in the art, e.g., naked DNA constructs, DNA vector based constructs, and/or viral vector and/or viral based constructs to express nucleic acids encoding, for example, mTOR, MYC, NOTCH or Atoh1 protein or modulators thereof. In certain embodiments, a single DNA construct expressing MYC and NOTCH or NICD as two separate genes can be delivered into the inner ear of a subject. In certain embodiments, a single DNA construct expressing MYC and NOTCH or NICD and Atoh1 as three separate genes can be delivered into the inner ear of a subject.

Exemplary expression constructs can be formulated as a pharmaceutical composition, e.g., for administration to a subject. DNA constructs and the therapeutic use of such constructs are well known to those of skill in the art (see, e.g. Chiarella et al. (2008) Recent Patents Anti-Infect. Drug Disc. 3: 93-101; Gray et al. (2008) Expert Opin. Biol. Ther. 8:911-922; Melman et al. (2008) Hum. Gene Ther. 17: 1165-1176). Naked DNA constructs typically include one or more therapeutic nucleic acids (e.g., DNA encoding MYC and/or NOTCH) and a promoter sequence. A naked DNA construct can be a DNA vector, commonly referred to as pDNA. Naked DNA typically does not integrate into chromosomal DNA. Generally, naked DNA constructs do not require, or are not used in conjunction with, the presence of lipids, polymers, or viral proteins. Such constructs may also include one or more of the non-therapeutic components described herein.

DNA vectors are known in the art and typically are circular double stranded DNA molecules. DNA vectors usually range in size from three to five kilo-base pairs (e.g., including inserted therapeutic nucleic acids). Like naked DNA, DNA vectors can be used to deliver and express one or more therapeutic proteins in target cells. DNA vectors do not integrate into chromosomal DNA.

Generally, DNA vectors include at least one promoter sequence that allows for replication in a target cell. Uptake of a DNA vector may be facilitated by combining the DNA vector with, for example, a cationic lipid, and forming a DNA complex. Typically, viral vectors are double stranded circular DNA molecules that are derived from a virus. Viral vectors typically are larger in size than naked DNA and DNA vector constructs and have a greater capacity for the introduction of foreign (i.e., not virally encoded) genes. Like naked DNA and DNA vectors, viral vectors can be used to deliver and express one or more therapeutic nucleic acids in target cells. Unlike naked DNA and DNA vectors, certain viral vectors stably incorporate themselves into chromosomal DNA. Typically, viral vectors include at least one promoter sequence that allows for replication of one or more vector encoded nucleic acids, e.g., a therapeutic nucleic acid, in a host cell. Viral vectors may optionally include one or more non-therapeutic components described herein. Advantageously, uptake of a viral vector into a target cell does not require additional components, e.g., cationic lipids. Rather, viral vectors transfect or infect cells directly upon contact with a target cell.

The approaches described herein include the use of retroviral vectors, adenovirus-derived vectors, and/or adeno-associated viral vectors as recombinant gene delivery systems for the transfer of exogenous genes in vivo, particularly into humans. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14, and other standard laboratory manuals.

Viruses that are used as transduction agents of DNA vectors and viral vectors such as adenoviruses, retroviruses, and lentiviruses may be used in practicing the present invention. Illustrative retroviruses include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus. As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; caprine arthritis-encephalitis virus (CAEV); equine infectious anemia virus (EIAV); feline immunodeficiency virus (FIV); bovine immune deficiency virus (BIV); and simian immunodeficiency virus (SIV).

In certain embodiments, an adenovirus can be used in accordance with the methods described herein. The genome of an adenovirus can be manipulated such that it encodes and expresses a gene product of interest but is inactivated in terms of its ability to replicate in a normal lytic viral life cycle. Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors.

Adeno-associated virus is a naturally occurring defective virus that requires another virus, such as an adenovirus or a herpes virus, as a helper virus for efficient replication and a productive life cycle. It is also one of the few viruses that may integrate its DNA into nondividing cells, and exhibits a high frequency of stable integration.

In various embodiments, one or more viral vectors that expresses a therapeutic transgene or transgenes encoding a polypeptide or polypeptides e.g., mTOR, Atoh1, NOTCH, MYC is administered by direct injection to a cell, tissue, or organ of a subject, in vivo.

In some embodiments of the invention, it may be desirable to use a cell, cell type, cell lineage or tissue specific expression control sequence to achieve cell type specific, lineage specific, or tissue specific expression of a desired polynucleotide sequence, for example, to express a particular nucleic acid encoding a polypeptide in only a subset of cell types, cell lineages, or tissues, or during specific stages of development. Illustrative examples of cell, cell type, cell lineage or tissue specific expression control sequences include, but are not limited to: an Atoh1 enhancer for all hair cells; a Pou4f3 promoter for all hair cell; a Myo7a promoter for all hair cells; a Hes5 promoter for vestibular supporting cells and cochlear inner phalangeal cells, Deiters cells and Pillar cells; and GFAP promoter for vestibular supporting cells and cochlear inner phalangeal cells, Deiters cells and Pillar cells.

Certain embodiments of the invention provide conditional expression of a polynucleotide of interest. For example, expression is controlled by subjecting a cell, tissue, organism, etc., to a treatment or condition that causes the polynucleotide to be expressed or that causes an increase or decrease in expression of the polynucleotide encoded by the polynucleotide of interest. Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al, 2003, *Gene*, 323: 67), the cumate inducible gene switch (WO 2002/088346), tetracycline-dependent regulatory systems, etc.

In certain embodiments, vectors comprise a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al, (1977) *Cell*, 11:223-232) and adenine phosphoribosyltransferase (Lowy et al, (1990) *Cell*, 22:817-823) genes which can be employed in tk- or aprt-cells, respectively.

In certain embodiments, DNA delivery may occur by use of liposomes, nanocapsules, microparticles, microspheres, lipid particles, vesicles, optionally mixing with cell penetrating polypeptides, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Duration of Delivery

The duration of mTOR, MYC, NOTCH and Atoh1 activation and PTEN inhibition can be varied to achieve a desired result. For example, it may be beneficial to expose a target cell to an mTOR activator, a PTEN inhibitor, a MYC protein or MYC activator and a NOTCH protein, NICD protein, or a NOTCH activator, for one to six days, one week, two weeks, three weeks, one month, three months, six months, nine months, one year, two years or more. Alternatively, when MYC is increased by constitutive activation (e.g., using an adenovirus to overexpress MYC), the duration of increased MYC activity can be controlled by administering a MYC inhibitor following administration of a MYC protein or a MYC activator. Inhibiting MYC activity after a period of increased MYC activity can be used to control proliferation, promote cell survival, and avoid tumorigenesis.

Similarly, the duration of increased mTOR activity can be controlled by administering an mTOR activator.

Route of Administration and Formulation

The route of administration will vary depending on the disease being treated. Hair cell loss, sensorineural hearing loss, and vestibular disorders can be treated using direct therapy using systemic administration and/or local administration. In certain embodiments, the route of administration can be determined by a subject's health care provider or clinician, for example following an evaluation of the subject.

The invention provides (i) a composition for use in proliferating or regenerating a cochlear or a utricular hair cell, (ii) a composition for use in proliferating or regenerating a cochlear or a utricular supporting cell, (iii) a composition for use in reducing the loss of, maintaining, or promoting hearing in a subject, and (iv) a composition for use in reducing the loss of, maintaining, or promoting vestibular function in a subject. Accordingly, the invention provides a first composition comprising an agent, for example, each of the agents discussed hereinabove, for example, an agent that increases mTOR expression or activity, MYC activity and/or an agent that increases NOTCH activity within a hair or supporting cell, either alone or in combination with a pharmaceutically acceptable carrier for use in each of the foregoing approaches. In certain embodiments, PTEN is administered as a component of the composition comprising an mTOR activator. In certain embodiments the mTOR activator and PTEN inhibitor are administered separately. In addition, the invention provides a second composition comprising an agent, for each of the agents discussed hereinabove, for example, an agent that reduces or inhibits MYC activity and/or an agent that reduces or inhibits NOTCH activity within a hair or supporting cell, either alone or in combination with in a pharmaceutically acceptable carrier for use in each of the foregoing approaches. When supporting cells are regenerated, the invention provides a third composition comprising an agent, for example, an agent for increasing Atoh1 activity, to induce trans differentiation of a proliferated supporting cell into a hair cell.

In addition, it is contemplated that the mTOR protein or activator, PTEN inhibitor, MYC protein or activator and/or the NOTCH protein, NICD protein, or NOTCH activator, and/or Atoh1 protein or activator can be formulated so as to permit release of one or more proteins and/or activators over a prolonged period of time. A release system can include a matrix of a biodegradable material or a material, which releases the incorporated active agents. The active agents can be homogeneously or heterogeneously distributed within a release system. A variety of release systems may be useful in the practice of the invention, however, the choice of the appropriate system will depend upon the rate of release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic.

In certain embodiments, the agents can be administered to a subject, e.g., a subject identified as being in need of treatment for hair cell loss, using a systemic route of administration. Systemic routes of administration can include, but are not limited to, parenteral routes of administration, e.g., intravenous injection, intramuscular injection, and intraperitoneal injection; enteral routes of administration, e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

Alternatively or in addition, the agents can be administered to a subject, e.g., a subject identified as being in need of treatment for hair cell loss, using a local route of administration. Such local routes of administration include administering one or more compounds into the ear of a subject and/or the inner ear of a subject, for example, by injection and/or using a pump.

In certain embodiments, the agents may be injected into the ear (e.g., auricular administration), such as into the luminae of the cochlea (e.g., the Scala media, Sc vestibulae, and Sc tympani). For example, the agents can be administered by intratympanic injection (e.g., into the middle ear), and/or injections into the outer, middle, and/or inner ear. Such methods are routinely used in the art, for example, for the administration of steroids and antibiotics into human ears. Injection can be, for example, through the round window of the ear or through the cochlea capsule.

In other embodiments, the agents can be delivered via nanoparticles, for example, protein-coated nanoparticles. Nanoparticles can be targeted to cells of interest based on cell-type specific receptor affinity for ligands coating the nanoparticles. The dosage of the agent can be modulated by regulating the number of nanoparticles administered per dose.

Alternatively, the agent may be administered to the inner ear using a catheter or pump. A catheter or pump can, for example, direct the agent into the cochlea luminae or the round window of the ear. Exemplary drug delivery systems suitable for administering one or more compounds into an ear, e.g., a human ear, are described in U.S. Patent Publication No. 2006/0030837 and U.S. Pat. No. 7,206,639. In certain embodiments, a catheter or pump can be positioned, e.g., in the ear (e.g., the outer, middle, and/or inner ear) of a subject during a surgical procedure.

Alternatively or in addition, the agents can be delivered in combination with a mechanical device such as a cochlea implant or a hearing aid, which is worn in the outer ear.

In certain embodiments, the modes of administration described above may be combined in any order and can be simultaneous or interspersed. For example, the agents may be administered to a subject simultaneously or sequentially. It will be appreciated that when administered simultaneously, the agents may be in the same pharmaceutically acceptable carrier (e.g., solubilized in the same viscoelastic carrier that is introduced into the inner ear) or the two agents may be dissolved or dispersed in separate pharmaceutical carriers, which are administered at the same time. Alternatively, the agents may be provided in separate dosage forms and administered sequentially.

Delivery of Agents to Hair Cells and Supporting Cells Ex Vivo

It is understood that the concepts for delivering agents of interest to hair cells and supporting cells in vivo can also apply to the delivery of the agents of interest to hair cells and supporting cells ex vivo. The hair cells and supporting cells can be harvested and cultured using techniques known and used in the art. The agents (protein expression vectors, activators and inhibitors (for example, as discussed above)) can then be contacted with the cultured hair cells or supporting cells to induce the cells to reenter the cell cycle, and proliferate. Thereafter, once the cells have proliferated, the MYC and NOTCH activities can be inhibited using appropriate inhibitors, for example, those discussed above. The resulting hair cells can then be maintained in culture for any number of uses, including, for example, to study the biological, biophysical, physiological and pharmacological characteristics of hair cells and/or supporting cells. Alternatively, the resulting hair cells can then be implanted in to the inner ear of a recipient using standard surgical procedures.

In certain embodiments, suitable cells can be derived from a mammal, such as a human, mouse, rat, pig, sheep, goat, or non-human primate. In certain embodiments, the cells can be harvested from the inner ear of a subject, and cells can be obtained from the cochlea organ of Corti, the modiolus (center) of the cochlea, the spiral ganglion of the cochlea, the vestibular sensory epithelia of the saccular macula, the utricular macula, or the cristae of the semicircular canals. Alternatively or in addition, methods include obtaining tissue from the inner ear of the animal, where the tissue includes at least a portion of the utricular maculae.

Tissue isolated from a subject can be suspended in a neutral buffer, such as phosphate buffered saline (PBS), and subsequently exposed to a tissue-digesting enzyme (e.g., trypsin, leupeptin, chymotrypsin, and the like) or a combination of enzymes, or a mechanical (e.g., physical) force, such as trituration, to break the tissue into smaller pieces. Alternatively, or in addition, both mechanisms of tissue disruption can be used. For example, the tissue can be incubated in about 0.05% enzyme (e.g., about 0.001%, 0.01%, 0.03%, 0.07%, or 1.0% of enzyme) for about 5, 10, 15, 20, or 30 minutes, and following incubation, the cells can be mechanically disrupted. The disrupted tissue can be passed through a device, such as a filter or bore pipette, that separates a stem cell or progenitor cell from a differentiated cell or cellular debris. The separation of the cells can include the passage of cells through a series of filters having progressively smaller pore size. For example, the filter pore size can range from about 80 µm or less, about 70 µm or less, about 60 µm or less, about 50 µm or less, about 40 µm or less, about 30 µm or less, about 35 µm or less, or about 20 µm or less.

Partially and/or fully differentiated cells, e.g., generated by the methods described above, can be maintained in culture for a variety of uses, including, for example, to study the biological, biophysical, physiological and pharmacological characteristics of hair cells and/or supporting cells. Cell cultures can be established using inner ear cells from subjects with hearing loss and/or loss in vestibular function to develop potential treatments (e.g., to screen for drugs effective in treating the hearing loss and/or loss in vestibular function). Further, the methods of the present invention can be used in combination with induced pluripotent stem (iPS) cell technology to establish cell lines (e.g., hair cell lines and/or supporting cell lines). For example, fibroblasts from a subject with hearing loss can be induced to form iPS cells using known techniques (see, for example, Oshima et al. (2010) *Cell*, 141(4):704-716).

However, because the numbers of cells generated using iPS cell technology is limited, the methods provided herein can be used in combination with iPS cell technology to produce sufficient numbers of cells to establish cell lines (e.g., hair cell lines and/or supporting cell lines).

Partially and/or fully differentiated cells, e.g., generated by the methods described above, can be transplanted or implanted, such as in the form of a cell suspension, into the ear by injection, such as into the luminae of the cochlea. Injection can be, for example, through the round window of the ear or through the bony capsule surrounding the cochlea. The cells can be injected through the round window into the auditory nerve trunk in the internal auditory meatus or into the scala tympani. In certain embodiments, the cells described herein can be used in a cochlea implant, for example, as described in U.S. Patent Publication No. 2007/0093878.

To improve the ability of transplanted or implanted cells to engraft, cells can be modified prior to differentiation. For example, the cells can be engineered to overexpress one or more anti-apoptotic genes. The Fak tyrosine kinase or Akt genes are candidate anti-apoptotic genes that can be used for this purpose; overexpression of FAK or Akt can prevent cell death in spiral ganglion cells and encourage engraftment when transplanted into another tissue, such as an explanted organ of Corti (see, for example, Mangi et al., (2003) *Nat. Med.* 9: 1195-201). Neural progenitor cells overexpressing $a_v\beta3$ integrin may have an enhanced ability to extend neurites into a tissue explant, as the integrin has been shown to mediate neurite extension from spiral ganglion neurons on laminin substrates (Aletsee et al., (2001) *Audiol. Neu. Ootol.* 6:57-65). In another example, ephrinB2 and ephrinB3 expression can be altered, such as by silencing with RNAi or overexpression with an exogenously expressed cDNA, to modify EphA4 signaling events. Spiral ganglion neurons have been shown to be guided by signals from EphA4 that are mediated by cell surface expression of ephrin-B2 and -B3 (Brors et al., (2003) *J. Comp. Neurol.* 462:90-100). Inactivation of this guidance signal may enhance the number of neurons that reach their target in an adult inner ear. Exogenous factors such as the neurotrophins BDNF and NT3, and LIF can be added to tissue transplants to enhance the extension of neurites and their growth towards a target tissue in vivo and in ex vivo tissue cultures. Neurite extension of sensory neurons can be enhanced by the addition of neurotrophins (BDNF, NT3) and LIF (Gillespie et al. (2010) *Neuro. Report* 12:275-279).

Measurement of mTOR, PTEN, MYC, NOTCH or Atoh1 Activity in Target Cells

The methods and compositions described herein can be used to induce cells, e.g., adult mammalian inner ear cells, to reenter the cell cycle and proliferate. For example, the number of hair cells can be increased about 2-, 3-, 4-, 6-, 8-, or 10-fold, or more, as compared to the number of hair cells before treatment. The hair cell can be induced to reenter the cell cycle in vivo or ex vivo. It is contemplated that using these approaches it may be possible to improve the hearing of a recipient. For example, using the methods and compositions described herein, it may be possible to improve the hearing of a recipient by at least about 5, 10, 15, 20, 40, 60, 80, or 90% relative to the hearing prior to the treatment. Tests of auditory or vestibular function also can be performed to measure hearing improvement.

Cells that have been contacted with (i) an mTOR activator, (ii) PTEN inhibitor, (iii) a MYC protein or MYC activator and/or (iv) a NOTCH protein, NICD protein or NOTCH activator, can be assayed for markers indicative of cell cycle reentry and proliferation. In one example, a cell can be assayed for incorporation of EdU (5-ethynyl-2'-deoxyuridine) followed sequentially by BrdU (5-bromo-2'-deoxyuridine) by using, for example, an anti-EdU antibody and an anti-BrdU antibody. Labelling by EdU and/or BrdU is indicative of cell proliferation. In addition, double labeling of EdU and BrdU can be used to demonstrate that a cell has undergone division at least two times. Alternatively or in addition, a cell can be assayed for the presence of phosphorylated histone H3 (Ph3) or aurora B, which are indicative of a cell that has reentered the cell cycle and is undergoing metaphase and cytokinesis.

Cell markers can also be used to determine whether a target cell, e.g., a hair cell or a supporting cell, has entered the cell cycle. Exemplary markers indicative of hair cells include Myo7a, Myo6, Prestin, Lhx3, Dner, espin, parvalbumin, and calretinin. Exemplary markers indicative of supporting cells include Sox2, S100a1, Prox1, Rps6, and Jag1. Double labeling of a cell cycle and/or proliferation marker and a cell-type molecule can be used to determine which cells have reentered the cell cycle and are proliferating.

In addition, neuronal markers, e.g., acetylated tubulin, neurofilament and CtBP2, can be used to detect neuronal structure, to determine whether proliferating hair cells are in contact with neurons. The presence of neuronal markers adjacent to or in contact with hair cells suggests that newly-generated hair cells have formed synapses with neurons (e.g., ganglion neurons) and that the hair cells are differentiated.

Where appropriate, following treatment, the subject, for example, a human subject, can be tested for an improvement in hearing or in other symptoms related to inner ear disorders. Methods for measuring hearing are well-known and include pure tone audiometry, air conduction, auditory brainstem response (ABR) and bone conduction tests. These exams measure the limits of loudness (intensity) and pitch (frequency) that a human can hear. Hearing tests in humans include behavioral observation audiometry (for infants to seven months), visual reinforcement orientation audiometry (for children 7 months to 3 years) and play audiometry for children older than 3 years. Oto-acoustic emission testing can be used to test the functioning of the cochlea hair cells, and electro-cochleography provides information about the functioning of the cochlea and the first part of the nerve pathway to the brain. In certain embodiments, treatment can be continued with or without modification or can be stopped.

Modulators

In some embodiments, the modulator is a therapeutic agent for delivery to a specific target. The target can be any desired intracellular target. In some embodiments, the target is a nucleic acid sequence or gene. In embodiments where it is desired to manipulate, modulate or edit a gene, the modulator is a gene or genome editing agent. In some embodiments, the gene editing agents comprise: transcriptional activators, transcriptional repressors, transcription factors, enhancer modulating molecules, recombinases, nucleases, nucleic acid binding-proteins, nucleic acid binding-polynucleotides or oligonucleotides, DNA-binding proteins or DNA-binding nucleic acids, or combinations thereof. In some embodiments, the target is a protein or peptide. Accordingly, in some embodiments, the modulator comprises one or more gene editing agents, transcriptional modulators, translational modulators, post-translational modulators, and/or modulators that regulate protein expression, function, activity or combinations thereof.

In some embodiments, the modulators comprise: oligonucleotides, polynucleotides, proteins, peptides, peptide nucleic acids (PNA), synthetic molecules or combinations thereof. In some embodiments, the oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), a short interfering RNA (siRNA), a micro, interfering RNA (miRNA), a small, temporal RNA (stRNA), a short, hairpin RNA (shRNA), mRNA, nucleic acid sequences comprising one or more modified nucleobases or backbones, or combinations thereof. The modulators also comprise one or more proteins or peptides which are cationic, anionic or are neutrally charged. Examples of proteins include without limitation: enzymes, hormones, chemotherapeutic agents, immunotherapeutic agents, genome or gene editing agents, synthetic molecules or combinations thereof. The gene or genome editing agents comprise: transcriptional activators, transcriptional repressors, recombinases, nucleases, DNA-binding proteins or nucleic acids, or combinations thereof. In some embodiments, the gene editing agents comprise: transcriptional activators, transcriptional repressors, transcription factors, enhancer modulating molecules, recombinases, nucleases, nucleic acid binding-proteins, nucleic acid binding-polynucleotides or oligonucleotides, DNA-binding proteins or DNA-binding nucleic acids, or combinations thereof.

In some embodiments, a liposome encapsulating one or more modulators or compositions embodied herein comprises a liposome, a nanoliposome, a niosome, a microsphere, a nanosphere, a nanoparticle, a micelle, or an archaeosome.

Modified Proteins or Peptides: The modulators may be hybrid proteins comprising a polypeptide or fragment thereof may be linked to other types of polypeptides. In addition, the additional polypeptide can be a signal peptide, or targeting peptide, etc.

In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility of the polypeptide. In some embodiments sites are selected for substitution with a naturally encoded or non-natural amino acid in addition to another site for incorporation of a non-natural amino acid for the purpose of increasing the polypeptide solubility following expression in recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport through tissues or cell membranes, prodrug release or activation, size reduction, or other traits of the polypeptide.

The methods and compositions described herein include incorporation of one or more non-natural amino acids into a polypeptide. One or more non-natural amino acids may be incorporated at one or more particular positions which does not disrupt activity of the polypeptide. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, including but not limited to agonists, super-agonists, partial agonists, inverse agonists, antagonists, receptor binding modulators, receptor activity modulators, modulators of binding to binder partners, binding partner activity modulators, binding partner conformation modulators, dimer or multimer formation, no change to activity or property compared to the native molecule, or manipulating any physical or chemical property of the polypeptide such as solubility, aggregation, or stability. For example, locations in the polypeptide required for biological activity of a polypeptide can be identified using methods including, but not limited to, point mutation analysis, alanine scanning or homolog scanning methods. Residues other than those identified as critical to biological activity by methods including, but not limited to, alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to make serial substitutions in each position on the polypeptide chain with a non-natural amino acid and observe the effect on the activities of the polypeptide.

Any means, technique, or method for selecting a position for substitution with a non-natural amino acid into any polypeptide is suitable for use in the methods, techniques and compositions described herein.

Modified Oligonucleotides: Examples of some oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, modified oligonucleotides comprise those with phosphorothioate backbones and those with heteroatom backbones, $CH_2$—NH—O—$CH_2$, CH, —$N(CH_3)$—O—$CH_2$ [known as a methylene(methylimino) or MMI backbone], $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones, wherein the native phosphodiester backbone is represented as O—P—O—CH). The amide backbones disclosed by De Mesmaeker et al. *Acc. Chem. Res.* 1995, 28:366-374) are also embodied herein. In some embodiments, the oligonucleotides having morpholino backbone structures (Summerton and Weller, U.S. Pat. No. 5,034,506), peptide nucleic acid (PNA) backbone wherein the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497). Oligonucleotides may also comprise one or more substituted sugar moieties. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-'7'7; Gebeyehu, G., et al. *Nucl*. *Acids Res*. 1987, 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., *Proc*. *Natl*. *Acad*. *Sci*. *USA* 1989, 86, 6553), cholic acid (Manoharan et al. *Bioorg*. *Med*. *Chem*. *Let*. 1994, 4, 1053), a thioether, e.g., hexyl-S-tritylthiol (Manoharan et al. *Ann*. *N.Y*. *Acad*. *Sci*. 1992, 660, 306; Manoharan et al. *Bioorg*. *Med*. *Chem*. Let. 1993, 3, 2765), a thiocholesterol (Oberhauser et al., *Nucl*. *Acids Res*. 1992, 20, 533), an aliphatic chain, e.g., dodecandiol or undecyl residues (Saison-Behmoaras et al. *EMBO J*. 1991, 10, 111; Kabanov et al. *FEBS Lett*. 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett*. 1995, 36, 3651; Shea et al. *Nucl*. *Acids Res*. 1990, 18, 3777), a polyamine or a polyethylene glycol chain (Manoharan et al. *Nucleosides* & *Nucleotides* 1995, 14, 969), or adamantane acetic acid (Manoharan et al. *Tetrahedron Lett*. 1995, 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

Labeled Molecules: In another preferred embodiment, the modulators can be labeled. Uses include therapeutic and imaging for diagnostic and prognostic purposes. The label may be a radioactive atom, an enzyme, or a chromophore moiety. Methods for labeling antibodies have been described, for example, by Hunter and Greenwood, *Nature,* 144:945 (1962) and by David et al. *Biochemistry* 13:1014-1021 (1974). Additional methods for labeling antibodies have been described in U.S. Pat. Nos. 3,940,475 and 3,645,090. Methods for labeling oligonucleotide probes have been described, for example, by Leary et al. *Proc*. *Natl*. *Acad*. *Sci*. *USA* (1983) 80:4045; Renz and Kurz, *Nucl*. *Acids Res*. (1984) 12:3435; Richardson and Gumport, *Nucl*. *Acids Res*. (1983) 11:6167; Smith et al. *Nucl*. *Acids Res*. (1985) 13:2399; and Meinkoth and Wahl, *Anal*. *Biochem*. (1984) 138:267.

The label may be radioactive. Some examples of useful radioactive labels include $^{32}P$, $^{125}I$, $^{131}I$, and $^{3}H$. Use of radioactive labels have been described in U.K. 2,034,323, U.S. Pat. Nos. 4,358,535, and 4,302,204.

Some examples of non-radioactive labels include enzymes, chromophores, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), β-galactosidase (fluorescein β-D-galactopyranoside), and alkaline phosphatase (5-bromo-4-chloro-3-indolyl phosphate/nitro blue tetrazolium). The use of enzymatic labels has been described in U.K. 2,019,404, EP 63,879, and by Rotman, *Proc*. *Natl*. *Acad*. *Sci*. *USA,* 47, 1981-1991 (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

The labels may be conjugated to the modulators by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate. Alternatively, labels such as enzymes and chromophores may be conjugated to the antibodies or nucleotides by means of coupling agents, such as dialdehydes, carbodiimides, dimaleimides, and the like.

Kits

In yet another aspect, the invention provides kits for regeneration of inner ear cells or treatment of hearing loss.

In one embodiment, a kit comprises: (a) modulators of mTOR, MYC, NOTCH, Atoh1, PTEN or any combinations thereof, and (b) instructions to administer to cells or an individual a therapeutically effective amount of the composition. In some embodiments, the kit may comprise pharmaceutically acceptable salts or solutions for administering the composition.

Optionally, the kit can further comprise instructions for suitable operational parameters in the form of a label or a separate insert. For example, the kit may have standard instructions informing a physician or laboratory technician to prepare a dose of modulators.

Optionally, the kit may further comprise a standard or control information so that a patient sample can be compared with the control information standard to determine if the test amount of modulator is a therapeutic amount consistent with for example, treating deafness in a patient.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, applicants do not admit any particular reference is "prior art" to their invention. Embodiments of inventive compositions and methods are illustrated in the following examples.

EXAMPLES

Example 1: mTOR is Downstream and Involved in the MYC/NICD Pathway and is Important in Renewed Proliferation and Hair Cell Regeneration in Adult/Mature Mammalian Inner Ear It was hypothesized that to achieve cell cycle re-entry in adult cochlea, mature cells need to be reprogrammed to re-gain the properties similar to young inner ear, which could allow them to respond to growth signals for proliferation. The inventor previously identified MYC as a proliferation master gene in zebrafish hair cell regeneration. Studies have shown NOTCH1 is a potent progenitor gene capable of reprograming non-sensory cells and converting them into pro-sensory fate in embryonic development. The combinatory effect of MYC and NOTCH1 activation in induction of proliferation in adult mouse cochlea in vitro and in vivo was studied.

Methods

Whole cochlea explant organ culture and microinjection into adult cochlea were used for the study in vitro and in vivo, respectively. NOTCH1 and c-MYC were activated in adult wild type mice by virus-mediated delivery, or in adult doxycycline-inducible rtTA/tet-MYC/tet-NICD transgenic mice through supplement of doxycycline in vitro and in vivo. EdU and BrdU incorporation was used to study proliferation. Lineage tracing using Sox2-promoter-driven Cre mice (Sox2-CreER) crossed with the tdTomato (tdT) reporter mice was conducted to identify the origin of proliferating cells. The mechanisms underlying reprograming were studied by qRT-PCR, immunolabeling and the effectors that modulate mTOR pathway. Survival was studied by analysis of apoptosis.

Results

MYC and NOTCH have been shown to interact with the mTOR signaling pathway". It was hypothesized that the reprogramming effect in adult cochlea by MYC/NICD may be mediated in part by the mTOR pathway. Prominent production of phospho-rpS6 (p-rpS6) was observed, an mTOR effector, in Dox-treated adult rtTA/tet-Myc/tet-NICD cochlea in culture (FIGS. 1A, 1C-1C") including dividing SCs (SOX2$^+$/EdU$^+$/p-rpS6$^+$, arrows, FIGS. 1C-1C"), but not in freshly dissected adult rtTA/tet-Myc/tet-NICD cochlea (FIGS. 1B-1B"). To determine the role of mTOR in MYC/NOTCH-mediated proliferation, Dox-treated adult rtTA/tet-Myc/tet-NICD cochlea culture were incubated with rapamycin, a well-known mTOR inhibitor. The p-rpS6 signal was virtually eliminated by rapamycin despite Dox treatment (FIGS. 1D-1D", 1E). Rapamycin treatment significantly reduced the number of EdU cells induced by Myc/NICD co-activation (FIGS. 1D-1D", 1F). The data strongly supported that mTOR is downstream of MYC/NICD and is required in MYC/NICD-mediated proliferation.

To study if mTOR plays a role in HC regeneration in adult cochlea, the number of regenerated HCs in Dox-treated adult rtTA/tet-Myc/tet-NICD *cochleae* infected by ad-Atoh1, with or without rapamycin treatment, were compared (FIG. 1G). Rapamycin treatment significantly reduced the number of regenerated HCs in the sensory epithelium or the limbus regions (FIGS. 1H-1J), supporting that mTOR is important for HC regeneration.

Figures 1K, 1L, 1M, 1N, 1O:
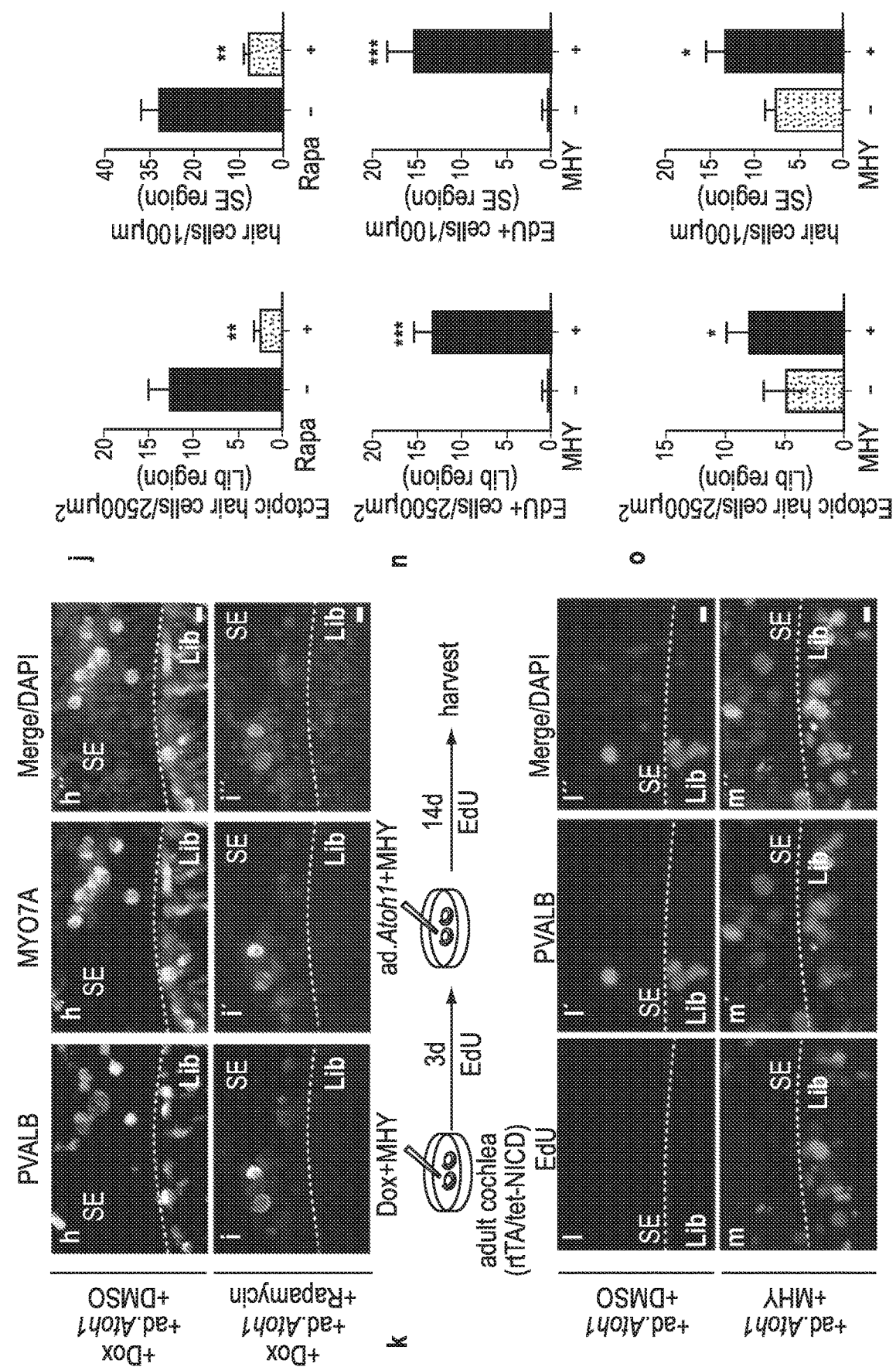

The prominent roles in proliferation and cell growth by mTOR provided evidence that it may compensate for part of the MYC functions. To determine if mTOR activation is sufficient to replace MYC to induce proliferation in adult cochlea, mTOR was activated in Dox-treated rtTA/tet-NICD adult cochlea culture by MHY1485, a small molecule mTOR activator[8] (FIG. 1K). EdU cells were observed in the sensory epithelium and the limbus regions after MHY1485 treatment, but not in control rtTA/tet-NICD cochlea exposed to Dox alone (FIGS. 1L-1N). The number of EdU cells was fewer after NICD activation and MHY1485 treatment than Myc/NICD co-activation (FIG. 1C'), indicating that mTOR partially compensates for MYC function in renewed proliferation. NOTCH activation by Dox in the rtTA/tet-NICD adult mice with MYH1485 treatment resulted in more HC regeneration by ad-Atoh1 than by Dox-induced NOTCH activation and ad-Atoh1 infection in cultured rtTA/tet-NICD adult cochlea (FIGS. 1L-1M", 1O), providing evidence that MHY1485 and NICD work synergistically to promote HC regeneration.

Figures 2A, 2B, 2C:
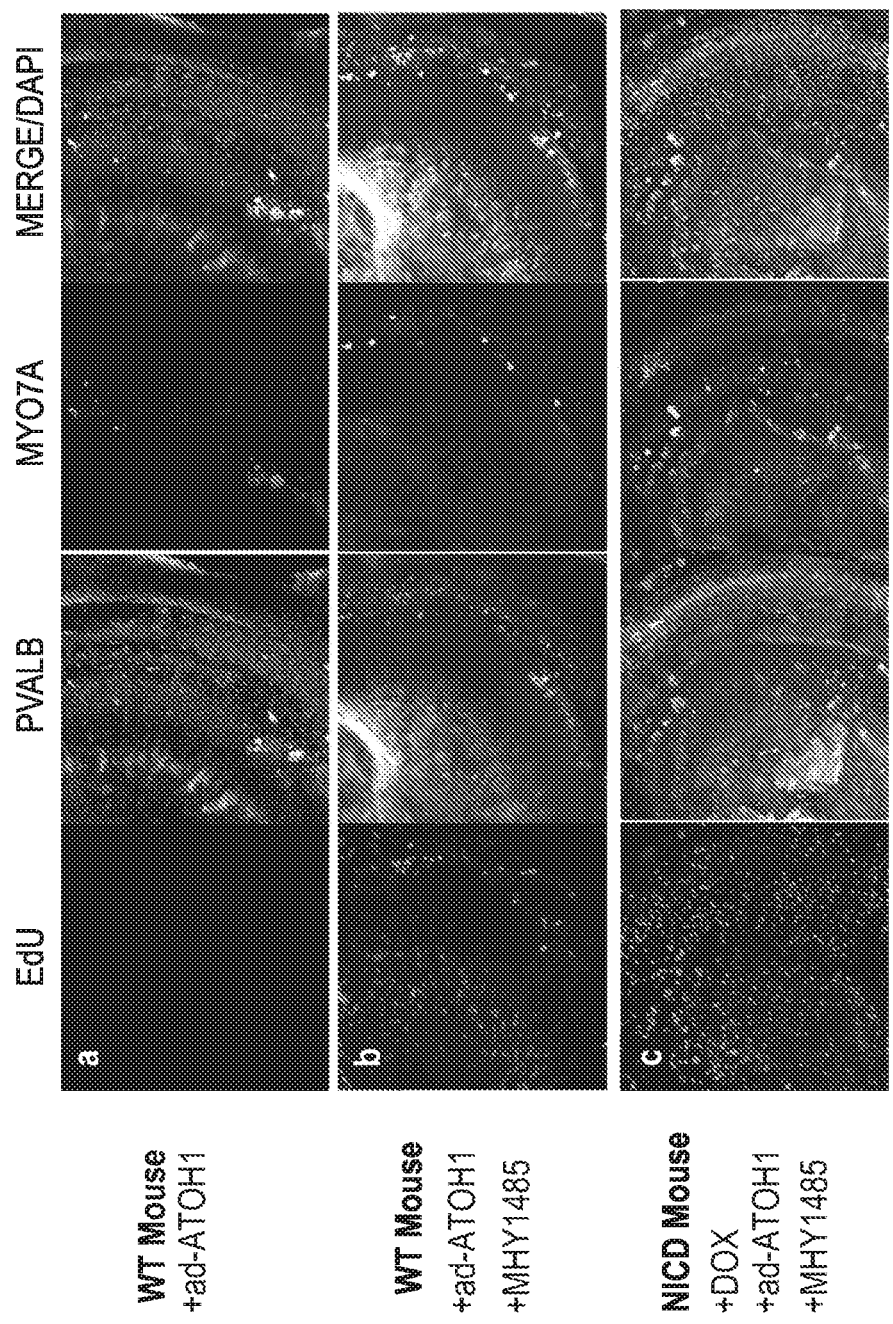
FIGS. 2A-2C are fluorescent stains demonstrating that activation of mTOR by MHY1482 induced renewed proliferation and enhanced hair cell regeneration in adult mouse cochlea in vitro.

To evaluate if mTOR is sufficient to induce proliferation, wildtype adult mouse cochlea were cultured and treated with MYH1485 to activate mTOR pathway followed by ad-Atoh1 infection for hair cell regeneration. Abundant EdU labeled cochlear cells were found in the MHY1485 treated cochlea but not in the cochlea only infected with Atoh1 (FIGS. 2A, 2B). More hair cells were regenerated in the MHY1485+ad-Atoh1 treated cochlea than ad-Atoh1 infected cochlea. Thus activation of mTOR by MHY1485 is sufficient to induce proliferation in adult/mature cochlea and it improves hair cell regeneration efficiency mediated by Atoh1. In adult rtTA/tet-NICD cochlea with MHY1485 and ad-Atoh1 treatment, we observed most proliferating cells (EdU$^+$) and most regenerated hair cells (PVALB$^+$/MYO7A$^+$) (FIG. 2C), again an indication of synergistic interaction between mTOR and NOTCH in renewed proliferation and hair cell regeneration.

CONCLUSION

It was demonstrated that co-activation MYC and NOTCH1 leads to cell cycle re-entry shown by EdU and BrdU incorporation in adult cochlea in vitro and in vivo. Lineage tracing shows diverse cochlear cell types, including pillar cells, Deiters cells, Hensen cells, Claudius cells, cells from limbus region and from stria vascularis are capable of renewed proliferation. Inner hair cells are induced to divide. Study with specific markers, including Ki67, pH3, Aurora B as well as the mitotic figure by the spindle marker α-tubulin, shows that dividing cells undergo DNA synthesis and different phases of proliferation and complete cell cycle. Renewed proliferation leads to increase in cell number. A majority of the proliferating cells are MYC/NICD double positive and maintain their identities after mitosis by expressing respective cellular markers. Survival of proliferating cells depends on duration of MYC/NICD activation: transient MYC/NICD function results in long-term survival of proliferating cells whereas sustained MYC/NICD activation induces apoptosis. Reprogramming by MYC/NICD is shown by upregulation of inner ear progenitor genes such as Six1, Eya1, Gata3 and Isl1 in the adult cochleae, whereas the stem cell genes and differentiation genes were not. mTOR pathway is activated in the non-sensory epithelial region upon MYC/NICD activation, and inhibition of mTOR by puromycin suppresses proliferation in those regions, demonstrating mTOR is downstream of MYC/NICD and is required for renewed proliferation. Finally in aged inner ear (12 month) proliferation is induced, indicating the same mechanism can be used to reprogram cochlear cell types for proliferation irrespective of age. Renewed proliferation in fully mature mammalian cochlea provides the opportunities to regenerate diverse inner ear cell types (such as supporting cells and stria), opening the possibility using regeneration to treat some forms of deafness.

In summary: mTOR is downstream of MYC/NOTCH pathway and is necessary for MYC/NOTCH mediated proliferation in adult/mature inner ear; mTOR can replace part of the function of MYC. This is shown by renewed proliferation in adult/mature mammalian inner ear induced by activation of mTOR by a mTOR activator compound MYH1485 and NOTCH activation; mTOR activation alone is sufficient to induce proliferation in adult/mature mammalian inner ear; mTOR and NOTCH activation enhances proliferation as well as ATOH1-mediated hair cell regeneration, an indication of synergistic interaction between mTOR and NOTCH.

REFERENCES

1. Chan, S. M., Weng, A. P., Tibshirani, R., Aster, J. C. & Utz, P. J. Notch signals positively regulate activity of the mTOR pathway in T-cell acute lymphoblastic leukemia. *Blood* 110, 278-286 (2007).
2. Ge, W. & Ren, J. mTOR-STAT3-notch signalling contributes to ALDH2-induced protection against cardiac contractile dysfunction and autophagy under alcoholism. *J Cell Mol Med* 16, 616-626 (2012).
3. Gera, J. F. et al. AKT activity determines sensitivity to mammalian target of rapamycin (mTOR) inhibitors by regulating cyclin D1 and c-myc expression. *J Biol Chem* 279, 2737-2746 (2004).
4. Ladu, S. et al. E2F1 inhibits c-Myc-driven apoptosis via PIK3CA/Akt/mTOR and COX-2 in a mouse model of human liver cancer. *Gastroenterology* 135, 1322-1332 (2008).
5. Masui, K. et al. mTOR complex 2 controls glycolytic metabolism in glioblastoma through FoxO acetylation and upregulation of c-Myc. *Cell Metab* 18, 726-739 (2013).
6. Wang, Z. et al. Down-regulation of Notch-1 and Jagged-1 inhibits prostate cancer cell growth, migration and invasion, and induces apoptosis via inactivation of Akt, mTOR, and NF-kappaB signaling pathways. *J Cell Biochem* 109, 726-736 (2010).
7. Lamming, D. W. Inhibition of the Mechanistic Target of Rapamycin (mTOR)-Rapamycin and Beyond. *Cold Spring Harb Perspect Med* 6 (2016).
8. Choi, Y. J. et al. Inhibitory effect of mTOR activator MHY1485 on autophagy: suppression of lysosomal fusion. *PLoS One* 7, e43418 (2012)

What is claimed is:

1. A method of regenerating inner ear cells in mature mammalian cochlea in a subject in need thereof, comprising contacting the cochlea with an effective amount of sodium valproate (VPA) and at least one activator of mechanistic target of rapamycin (mTOR), selected from the group consisting of MHY1485, 3-benzyl-5-((2-nitrophenoxy) methyl) dihydrofuran-2(3H)-one (3BDO), salidroside, and polynucleotides encoding mTOR, sufficient to induce reprogramming, proliferation and regeneration of inner ear cells; thereby regenerating the inner ear cells in mature mammalian cochlea.

2. The method of claim 1, wherein the inner ear cells comprise: stria vascularis, hair cells, supporting cells or ganglion neurons.

3. The method of claim 1, further comprising administering one or more phosphatase and tensin homolog (PTEN) inhibitors, and/or Atonal Homolog 1 (Atoh1) activators, wherein the Atoh1 activators comprise β-catenin or Atoh1 polynucleotides.

4. The method of claim 3, wherein the one or more PTEN inhibitors comprise: bpV(phen), bpV(pic), VO-OHpic, SF1670, antibodies, antibody fragments, antisense oligonucleotides, or siRNAs.

5. A composition comprising: an effective amount of sodium valproate (VPA) and at least one activator of mechanistic target of rapamycin (mTOR), selected from the group consisting of MHY1485, 3-benzyl-5-((2-nitrophenoxy) methyl)dihydrofuran-2(3H)-one (3BDO), salidroside, and polynucleotides encoding mTOR.

6. The composition of claim 5, further comprising an effective amount of one or more phosphatase and tensin homolog (PTEN) inhibitors, and/or Atonal Homolog 1 (Atoh1) activators, wherein the Atoh1 activators comprise β-catenin or Atoh1 polynucleotides.

7. The composition of claim 6, wherein the one or more PTEN inhibitors comprise: bpV(phen), bpV(pic), VO-OHpic, SF1670, antibodies, antibody fragments, antisense oligonucleotides, or siRNAs.

* * * * *